United States Patent
Kumakhov

(10) Patent No.: US 7,315,757 B2
(45) Date of Patent: Jan. 1, 2008

(54) RADIOSCOPY USING $K_\alpha$ GADOLINIUM EMISSION

(76) Inventor: Muradin Abubekirovich Kumakhov, ul. Narodnogo Opolcheniya, d. 38, kv. 55, Moscow 123298 (RU)

(*) Notice: Subject to any disclaimer, the term of this patent is extended or adjusted under 35 U.S.C. 154(b) by 916 days.

(21) Appl. No.: 10/311,061

(22) PCT Filed: Apr. 16, 2001

(86) PCT No.: PCT/RU01/00149

§ 371 (c)(1),
(2), (4) Date: Dec. 16, 2002

(87) PCT Pub. No.: WO02/083238

PCT Pub. Date: Oct. 24, 2002

(65) Prior Publication Data

US 2004/0017889 A1    Jan. 29, 2004

(51) Int. Cl.
*A61B 6/00* (2006.01)
*A61B 5/05* (2006.01)

(52) U.S. Cl. ............... 600/427; 600/407; 600/431; 378/62; 378/64

(58) Field of Classification Search ............ 600/420, 600/431; 250/302, 303; 378/65, 62, 64
See application file for complete search history.

(56) References Cited

U.S. PATENT DOCUMENTS

| | | | | |
|---|---|---|---|---|
| 5,207,223 A | | 5/1993 | Adler | 128/653.1 |
| 5,497,008 A | * | 3/1996 | Kumakhov | 250/505.1 |
| 5,569,925 A | * | 10/1996 | Quinn et al. | 250/370.06 |
| 5,754,623 A | | 5/1998 | Seki | 378/65 |
| 5,846,519 A | | 12/1998 | Tweedle | 424/9.363 |
| 6,108,398 A | * | 8/2000 | Mazor et al. | 378/45 |
| 6,125,295 A | * | 9/2000 | Cash et al. | 600/431 |
| 2005/0245819 A1 | * | 11/2005 | Kumakhov | 600/427 |

FOREIGN PATENT DOCUMENTS

RU   2091093   9/1997

* cited by examiner

*Primary Examiner*—Brian L. Casler
*Assistant Examiner*—Crystal I Leach
(74) *Attorney, Agent, or Firm*—McDermott Will & Emery LLP

(57) ABSTRACT

The methods comprise detection of gadolinium in human tissues and organs by refining the position of malignant neoplasm and radiation treatment of the neoplasm in order to damage its cells. Refined position of the malignant neoplasm is determined by introducing gadolinium into the patient body and scanning part of the patient body in which the neoplasm is located. The scanning is performed by displacement of zone of radiation concentration created by intersection of several X-ray beams having radiation energy corresponding to K-edge of gadolinium atoms absorption. The refined information is acquired using detectors sensitive to $K_\alpha$-radiation of gadolinium atoms, to which secondary radiation is transported arising in zone of concentration. Scanning is performed of the region of the malignant neoplasm location utilizing the same means as in the first stage. Sources of X-ray radiation are switched with control means into elevated intensity mode, sufficient for radiation damage of the malignant neoplasm tissues.

34 Claims, 11 Drawing Sheets

RADIOSCOPY USING $K_\alpha$ GADOLINIUM EMISSION

FIELD OF THE INVENTION

The invention relates to the means for position determination of malignant neoplasms in the patient body and their exposure with the purpose of malignant neoplasm cells injury to X-ray radiation.

BACKGROUND OF THE INVENTION

Methods are known which provide for carrying out the preliminary preparation after diagnosis being established and decision made on radiation therapy application to the malignant neoplasm with the purpose of damaging its cells. In the course of preliminary preparation, linear dimensions, area and volume of pathological masses, organs and anatomic structures is determined and their positional relationship is described in quantitative terms for particular patient (see, for example: Radiation therapy of malignant tumors. Physician's handbook. Prof. E. S. Kiseleva, Ed., Moscow, "Meditsina" publishing house, 1996 [1], p.46-47). Principal task of the preliminary preparation lies in merging different data obtained in the course of the disease diagnosis and providing specialists effecting radiation treatment with topographic anatomical information on the site to be irradiated in the form allowing for development of irradiation program. In order to choose variants and parameters of irradiation program, it is necessary to know shape and dimensions of the malignant focus, its orientation in the body of patient, as well as relative position of surrounding organs and tissues, distance between the malignant focus and the most important in respect to radiation load distribution anatomical structures and critical organs. As a result of preliminary preparation and irradiation program development, in particular, specific points and areas are chosen on patient body surface, relative to which X-ray beams are oriented subsequently in the course of irradiation.

Principal disadvantage of the above combination of patient preparation to irradiation and irradiation proper lies in the fact of the stages being separated both in time and in space, in particular, due to that they are accomplished using different means. The irradiation (radiation treatment to damage the malignant neoplasm cells) is accomplished using directional sources of rather powerful X-ray radiation. As to roentgenoscopic investigation preceding the irradiation, it is made at substantially lower radiation intensities and, besides, constitutes usually only one of numerous methods used in combination: angiography, excretory urography, investigations of gastrointestinal tract, skeleton and cranial bones, and chest organs; radionuclide examinations of bones and liver; ultrasonic methods—echoscopy, echotomography, allowing visualization of abdominal cavity and pelvis organs and soft tissues; computerized tomography; magnetic resonance tomography, etc. As a consequence, it is extremely difficult to ensure high precision of radiation treatment, with the result of malignant focus tissues remaining partially unirradiated or intensive X-ray radiation being concentrated in the region exceeding the malignant focus in size. In the latter case, surrounding healthy tissues are damaged substantially stronger than at inevitable irradiation of healthy tissues located in the way of radiation to the malignant focus.

In realizing such technique, not only imprecision of the reference points selection and X-ray beams "aiming" during radiation treatment became manifest, but also variability of the internal organs location, and inaccuracy of patient accommodation during different seances of radiation treatment. Moreover, dose fractionation in itself, though caused by endeavor to avoid overirradiation of healthy tissues, results in vicious circle, because it is known that dose required for irreversible damage of the malignant focus, when applied in single exposure, is several times as less as the total dose required at fractionation [1, p.84, 91].

In a number of known technical solutions, special measures are taken to overcome this drawback, directed at exactness and stability enhancement of the patient positioning (see, for example, U.S. Pat. No. 5,983,424, publ. Nov. 16, 1999 [2]).

Another way to overcome said drawbacks lies in application of so called simulator—roentgenological apparatus similar in geometric and kinematical capabilities to the teleirradiation apparatus [1 p.55]. With simulator it is possible, without patient position changing, to "X-ray" him in different directions. During preliminary preparation patient is placed on the simulator table in a position, corresponding to that in which he will be during irradiation, and roentgenoscopy is performed. Using light crosshairs and relocatable roentgenocontrast threads, center and boundaries of irradiation volume are chosen, and plane is designated in which central axis of radiation beam will pass during radiation exposure.

However, none of such measures allow to avoid inaccuracies in the "aiming" of beams effecting radiation exposure on malignant neoplasm, caused by tumor growth. This factor turns out to be the most essential at lengthy treatment terms, when irradiation sessions are distanced in time from the moment of diagnostic examination of patient.

Technical solutions most close to the inventions proposed are disclosed in U.S. Pat. No. 5,207,223 (publ. May 4, 1993 [3]). In the methods (method of radiation exposure of malignant neoplasm and its constituent method of determination of refined location of malignant neoplasm) of this patent utilizing directed X-ray beams allowing to obtain images of patient tissues structure, such images are produced immediately before the radiation exposure and used in comparison with the results of previous diagnostic examinations to correct the irradiation program. At that, however, different beams are used for producing said images and for radiation treatment of malignant focus tissues, which allows not in principle to avoid mistakes in irradiating beams orientation.

Besides, operating principle of known methods and means is based on the use of information contained in shadow projections of tissues and organs through which X-ray radiation had passed. Therefore, information on the actual density of tissues and organs being of interest (in the given case—on density of tissues and organs in the presumable location of malignant focus) is distorted due to the presence of other tissues and organs in the way of "transmitting" radiation beam. At that, only high qualification of specialist carrying out the roentgenoscopy allows to differentiate image elements relating to malignant neoplasms. In case of projections overlapping of the neoplasm and some solid organs, unequivocal conclusion is difficult to make. It requires production of another image projection with different orientation of "transmitting" beam, which is associated with increase in irradiation dose. Effect of drawbacks of the group considered is diminished in the means realizing computed tomography principles, which entails not only complexity of corresponding technical means, but also rather high irradiation dose.

DISCLOSURE OF THE INVENTIONS

The technical result achieved with the inventions proposed related to the method of radiation treatment of malignant neoplasm with the purpose of damaging its cells, method of determination of refined malignant neoplasm location, and means for their realization, lies in eliminating the influence of abovementioned factor comprising inaccuracy of the beams "aiming" due to the use of one and the same X-ray beams both for determination of tissues structure and malignant focus location and radiation treatment proper of the malignant focus.

Another kind of the technical result achieved is reduction of the irradiation dose in the course of obtaining tissues structure images used for irradiation program correction, as well as reduction in irradiation dose of tissues surrounding region selected for radiation exposure. This result is achieved due to abandonment of "shadow" principle of the image acquisition. At that, simultaneously, abovementioned disadvantages inherent to this principle are eliminated without utilization of complex means applied in computed tomography.

Also without use of computed tomography unequivocal differentiation of the neoplasm is ensured. This is achieved due to the fact of tissues density ceasing to be sole criterion of the neoplasm differentiation.

The increase in the exactness of the malignant neoplasm location determination at the first stage facilitates decrease in healthy tissues and organs irradiation at the second stage.

Additional result achieved at the second stage consists in selective action of radiation predominantly on the malignant neoplasm.

The method proposed of radiation treatment of malignant neoplasm with the purpose of damaging its cells with X-ray beams, similar to known one mentioned above, is accomplished in two stages. At the first stage, malignant neoplasm image is acquired as a set of spatial coordinates of the points comprising current results of measurements differentiated as those belonging to the malignant neoplasm. After that, irradiation program is built up as an aggregate of X-ray radiation doses which should be supplied to different parts of the malignant neoplasm represented by fixed sets of points coordinates. After that, transition to the second stage is accomplished to realize the irradiation program generated.

To achieve the above kinds of technical result in the method proposed, gadolinium-containing preparation is introduced into patient organism at the first stage, as distinct from the known one. The preparation is introduced in the amount predetermined for the given patient, which is sufficient for consequent gadolinium detection in tissues affected by malignant neoplasm. Then, after expiration of time period predetermined for the given patient, which is sufficient for gadolinium accumulation in tissues affected by malignant neoplasm in the amount, which may be detected with the means used, X-ray radiation is concentrated in a zone located within part of the patient body containing the malignant neoplasm, including point to which current results of measurements are referenced. At that, radiation is used with energy corresponding to K-edge absorption of gadolinium atoms. Secondary radiation arising in said zone is transported to one or more detectors sensitive to $K_\alpha$-radiation of gadolinium atoms. At that, scanning is performed of the part of patient body containing the malignant neoplasm by mutual displacement of radiation concentration zone and body of patient. Detection of secondary radiation excited in zone irradiated is made by scanning within the limits of radiation concentration zone in its current position with field of view of one or more detectors sensitive to $K_\alpha$-radiation of gadolinium atoms, or by simultaneous registration with one or more of such secondary radiation detectors from all the zone of radiation concentration in its current position. In the moment of signal appearance at the output of any of detectors sensitive to $K_\alpha$-radiation of gadolinium atoms, parameters are fixed characterizing spatial position of zone irradiated and field of view of each detector sensitive to $K_\alpha$-radiation of gadolinium atoms with a signal detected at the output. Each of the regions in common for radiation concentration zone and fields of view of detectors sensitive to $K_\alpha$-radiation of gadolinium atoms with a signal detected at the output is registered as containing the malignant neoplasm cells. Then from aggregate of all such regions detected determination is carried out of the shape and refined location of the malignant neoplasm as a whole.

At the second stage, region of space occupied by the malignant neoplasm is scanned within body of patient, concentration of X-ray radiation being performed with the same means as in the first stage. The scanning is performed in such a way that the positions occupied by concentration zone would correspond to the parts of the malignant neoplasm represented with sets of points coordinates registered at the first stage. The irradiation program generated at the first stage is fulfilled by increasing X-ray radiation intensity in comparison with the first stage and controlling the duration of irradiation.

At that, increase in radiation intensity may be carried out with increase in emission bandwidth and/or its spectral density.

Concentration of X-ray radiation in zone comprising the point to which current results of measurements are related, situated within part of patient body containing the malignant neoplasm, may be effected, for example, with one or more collimators using corresponding number of spatially separated X-ray sources. At that, transportation of secondary radiation arising to one or more detectors sensitive to $K_\alpha$-radiation of gadolinium atoms may also be performed using one or more collimators, all the collimators being oriented in such a way that axes of their central channels would intersect in a point, to which current results of measurements are referenced.

It is possible also to achieve concentration of X-ray radiation in a zone comprising point, to which current results of measurements are referenced, situated within part of patient body containing the malignant neoplasm, using one or more X-ray half-lenses transforming divergent radiation from corresponding number of spatially separated X-ray sources into the quasi-parallel one. At that, transportation of the secondary radiation arising to one or more detectors sensitive to $K_\alpha$-radiation of gadolinium atoms is performed with one or more X-ray half-lenses focusing this radiation on the detectors sensitive to $K_\alpha$-radiation of gadolinium atoms, or forming quasi-parallel radiation, all the X-ray half-lenses being oriented in such a way that their optical axes would intersect in a point, to which current results of measurements are referenced.

Concentration of X-ray radiation in a zone comprising point, to which current results of measurements are referenced, situated within part of patient body containing the malignant neoplasm, may be effected also with one or more of X-ray half-lenses transforming divergent radiation from corresponding number of spatially separated X-ray sources into the quasi-parallel one, and transportation of secondary radiation arising to one or more detectors sensitive to $K_\alpha$-radiation of gadolinium atoms—with one or more X-ray lenses focusing this radiation on the detectors sensitive to $K_\alpha$-radiation of gadolinium atoms. At that, all the X-ray half-lenses and lenses are oriented in such a way that their optical axes would intersect in a point, to which current results of measurements are referenced.

In one of particular embodiments of the method proposed concentration of X-ray radiation in a zone comprising point, to which current results of measurements are referenced, situated within part of patient body containing the malignant neoplasm, is effected with several X-ray half-lenses transforming divergent radiation of the corresponding number of spatially separated sources into quasi-parallel one, and transportation of the secondary radiation arising to one or more detectors sensitive to $K_\alpha$-radiation of gadolinium atoms—with one or more collimators. At that, X-ray half-lenses and collimators are oriented in such a way that optical axes of all the X-ray half-lenses and central channel of all the collimators would intersect in a point, to which current results of measurements are referenced.

In another particular case, concentration of X-ray radiation in a zone comprising point, to which current results of measurements are referenced, situated within part of patient body containing the malignant neoplasm, is effected with one or more spatially separated X-ray sources and corresponding number of X-ray lenses focusing divergent X-ray radiation from each of the sources in a point, to which current results of measurements are referenced. In this case, transportation of the secondary radiation arising to one or more detectors sensitive to $K_\alpha$-radiation of gadolinium atoms is accomplished with X-ray lenses focusing this radiation on the detectors sensitive to $K_\alpha$-radiation of gadolinium atoms and having second focus in the point specified. In this particular case, additional technical result is achieved, consisting in possibility of the radiation treatment localization in regions of super small size with a small number of beams (even with one) in combination with low level of healthy tissues irradiation, thus allowing possibly to avoid fractionation of irradiation and in certain cases to perform radiation treatment to damage cells of small tumors in one session. Possibility of achievement of given kind of technical result is ensured by X-ray lenses utilization in the invention proposed.

In another particular case, concentration of X-ray radiation in a zone comprising point, to which current results of measurements are referenced, situated within part of patient body containing the malignant neoplasm, is effected with one or more spatially separated X-ray sources and corresponding number of X-ray lenses focusing divergent X-ray radiation from each of the sources in a point, to which current results of measurements are referenced. At that, transportation of the secondary radiation arising to one or more detectors sensitive to $K_\alpha$-radiation of gadolinium atoms is performed with collimators oriented in such a way that optical axes of their central channels would intersect in the point specified.

In the method proposed of the malignant neoplasm position determination using X-ray radiation beams, similar to the known method according to U.S. Pat. No. 5,207,223 [3], image of the malignant neoplasm is acquired in the form of aggregate of spatial coordinates of the points, to which current results of measurements are referenced.

As distinct from known method specified, in order to achieve the technical result mentioned above in the method proposed introduction of gadolinium-containing preparation into the organism of patient is accomplished in the amount predetermined for given patient, which is sufficient for subsequent detection of gadolinium in tissues affected with the malignant neoplasm. Then, after expiration of time period predetermined for the given patient, which is sufficient for gadolinium accumulation in tissues affected by malignant neoplasm in the amount, which may be detected, X-ray radiation is concentrated in a zone, comprising point to which current results of measurements are referenced, located within part of the patient body containing the malignant neoplasm. At that, radiation is used with energy corresponding to K-edge absorption of gadolinium atoms. Secondary radiation arising in said zone is transported to one or more detectors sensitive to $K_\alpha$-radiation of gadolinium atoms. At that, scanning is performed of the part of patient body containing the malignant neoplasm by mutual displacement of radiation concentration zone and body of patient. Detection of secondary radiation excited in zone irradiated is made by scanning within the limits of radiation concentration zone in its current position with field of view of one or more detectors sensitive to $K_\alpha$-radiation of gadolinium atoms, or by simultaneous registration with one or more of such secondary radiation detectors from all the zone of radiation concentration in its current position. In the moments of signals appearance at the output of any of detectors sensitive to $K_\alpha$-radiation of gadolinium atoms, parameters are registered characterizing spatial position of zone irradiated and field of view of each detector sensitive to $K_\alpha$-radiation of gadolinium atoms with a signal detected at the output. Each of the regions in common for radiation concentration zone and fields of view of detectors sensitive to $K_\alpha$-radiation of gadolinium atoms with a signal detected at the output is registered as containing the malignant neoplasm cells. Then from aggregate of all such regions registered determination is carried out of the shape and refined location of the malignant neoplasm as a whole.

In a particular embodiment of the method proposed for a position determination of the malignant neoplasm, concentration of X-ray radiation in a zone comprising point, to which current results of measurements are referenced, situated within part of patient body containing the malignant neoplasm, is effected with one or more collimators. At that, corresponding number of spatially separated X-ray sources is used, and transportation of the secondary radiation arising to one or more detectors sensitive to $K_\alpha$-radiation of gadolinium atoms is also accomplished using one or more collimators; all the collimators being oriented in such a way that their axes of central channels would intersect in a point, to which current results of measurements are referenced.

In another particular case, concentration of X-ray radiation in a zone comprising point, to which current results of measurements are referenced, situated within part of patient body containing the malignant neoplasm, is effected with one or more of X-ray half-lenses transforming divergent radiation of corresponding number of spatially separated X-ray sources into quasi-parallel one, and transportation of secondary radiation arising to one or more detectors sensitive to $K_\alpha$-radiation of gadolinium atoms—with one or more of X-ray half-lenses focusing said radiation on the detectors sensitive to $K_\alpha$-radiation of gadolinium atoms or forming quasi-parallel radiation. At that, all the X-ray half-lenses are oriented in such a way that their optical axes would intersect in a point, to which current results of measurements are referenced.

In yet another particular case, concentration of X-ray radiation in a zone comprising point, to which current results of measurements are referenced, situated within part of patient body containing the malignant neoplasm, is effected with one or more X-ray half-lenses transforming divergent radiation from corresponding number of spatially separated X-ray sources into quasi-parallel one, and transportation of secondary radiation arising to one or more detectors sensitive to $K_\alpha$-radiation of gadolinium atoms—with one or more X-ray lenses focusing said radiation on the detectors. At that, all the X-ray half-lenses and lenses are oriented in such a way that their optical axes would intersect in a point, to which current results of measurements are referenced.

In another particular case, concentration of X-ray radiation in a zone comprising point, to which current results of measurements are referenced, situated within part of patient body containing the malignant neoplasm, is effected using several X-ray half-lenses transforming divergent radiation from corresponding number of spatially separated sources into quasi-parallel one, and transportation of secondary radiation arising to one or more detectors sensitive to $K_\alpha$-radiation of gadolinium atoms—with one or more collimators. At that, X-ray half-lenses and collimators are oriented in such a way that optical axes of all the X-ray half-lenses and those of central channels of all the collimators would intersect in a point, to which current results of measurements are referenced.

Concentration of X-ray radiation in a zone comprising point, to which current results of measurements are referenced, situated within part of patient body containing the malignant neoplasm, may be also effected using one or more spatially separated X-ray sources and corresponding number of X-ray lenses focusing divergent X-ray radiation from each of the sources in a point, to which current results of measurements are referenced, and transportation of the secondary radiation arising to one or more detectors sensitive to $K_\alpha$-radiation of gadolinium atoms—using X-ray lenses focusing said radiation on the detectors and having second focus in the point specified.

Besides, it is possible to perform concentration of X-ray radiation in a zone comprising point, to which current results of measurements are referenced, situated within part of patient body containing the malignant neoplasm, utilizing one or more spatially separated X-ray sources and corresponding number of X-ray lenses focusing divergent X-ray radiation from each of the sources in a point, to which current results of measurements are referenced. Transportation of secondary radiation arising to one or more detectors sensitive to $K_\alpha$-radiation of gadolinium atoms in this case is accomplished using collimators oriented in such a way that optical axes of their central channels would intersect in the point specified.

Both methods proposed comprise as a constituent part a method of gadolinium presence detection in tissues of human body.

Detection of gadolinium in tissues of human body takes place indirectly during realization of traditional roentgenoscopic methods utilizing radiopaque contrast agents comprising gadolinium (see, for example, Russian Federation patents Nos. 2081881 and 2134067, U.S. Pat. Nos. 5,746, 995 and 5,846,519. However, these methods, including those realized by means of computed tomography, use information contained in shadow projections of tissues and organs, detection of gadolinium being not an objective of such methods. Due to this reason, reliability of conclusion on the gadolinium presence in this or that organ made from their images observed is small enough.

To ensure high reliability of gadolinium presence detection (and due to this—high reliability of localization of tissues and organs affected with the malignant neoplasm, in which accumulates gadolinium introduced into patient's body), X-ray radiation with energy corresponding to K-edge absorption of gadolinium atoms is concentrated in a zone of patient body, in which are located tissues and organs presumably containing gadolinium. Secondary radiation arising in this zone is transported to one or more detectors sensitive to $K_\alpha$-radiation of gadolinium atoms, and registration is performed of the secondary radiation excited in the zone irradiated by scanning within limits of the radiation concentration zone in its current position with a field of view of one or more detectors sensitive to $K_\alpha$-radiation of gadolinium atoms, or simultaneous registration with one or more of such detectors of the secondary radiation from all the zone of radiation concentration in its current position. In the moment of signal appearance at the output of any detector sensitive to $K_\alpha$-radiation of gadolinium atoms, parameters are registered which characterize spatial position of the zone irradiated and field of view of each of the detectors sensitive to $K_\alpha$-radiation of gadolinium atoms having a signal detected at the output, and each region in common for the radiation concentration zone and fields of vision of the detectors sensitive to $K_\alpha$-radiation of gadolinium atoms with signal detected at the output is registered as that containing gadolinium.

In one of the embodiments of this method, concentration of X-ray radiation in a zone of patient body comprising tissues and organs in which presumably gadolinium is contained, is performed utilizing one or more spatially separated X-ray sources and corresponding number of X-ray lenses focusing divergent X-ray radiation from each of the sources in a point, to which current results of measurements are referenced. In this case, transportation of secondary radiation arising to one or more detectors sensitive to $K_\alpha$-radiation of gadolinium atoms is accomplished using X-ray lenses focusing this radiation on the detectors sensitive to $K_\alpha$-radiation of gadolinium atoms and having second focus in the point specified.

In order to realize all the methods proposed, one and the same device may be used. This device, similar to abovementioned known device according to U.S. Pat. No. 5,207, 223 [3] for position determination of the malignant neoplasm and radiation exposure of the malignant neoplasm using X-ray radiation beams, comprises roentgenooptical system, means for mutual positioning of patient body and roentgenooptical system, and means for information processing and representation. At that, Roentgenooptical system comprises one or more X-ray sources with means for concentration of their radiation and one or more detectors with outlets being connected to the means for information processing and representation.

In order to achieve the abovementioned kinds of technical result, intrinsic to the inventions proposed, the X-ray sources belonging to the Roentgenooptical system of the device proposed, as distinct from known one, are made with possibility of generating radiation with energy corresponding to K-edge of gadolinium atoms absorption. Means for concentration of radiation from these sources are made and installed with possibility of concentrating the radiation from all the sources in a zone comprising a point, to which current results of measurements are referenced, situated inside the part of patient body containing the malignant neoplasm. Roentgenooptical system comprises also one or more means for transportation of secondary radiation arising in concentration zone, to the detectors sensitive to $K_\alpha$-radiation of gadolinium atoms, which are installed at the outlets of these means. The means for mutual positioning of patient body and Roentgenooptical system is connected to sensors for coordinates determination of a point, to which current results of measurements are referenced, located inside the part of patient body containing the malignant neoplasm, attached with their outputs to the means for information processing and representation. The latter is made with possibility of displaying boundaries of the malignant neoplasm, determined in the result of scanning by concentration zone of X-ray sources radiation of the part of patient body containing the malignant neoplasm with means for mutual positioning of the patient body and Roentgenooptical system.

To achieve damaging action on the malignant neoplasm cells, X-ray sources belonging to the Roentgenooptical system may be made with possibility of changing their radiation intensity, and the Roentgenooptical system comprises means for joint control of the radiation intensity of X-ray sources.

In one of embodiments of the device proposed, each of the means for concentration of their radiation in a zone comprising point, to which current results of measurements are referenced, and means for transportation of the secondary radiation arising in it to the detectors sensitive to $K_\alpha$-radiation of gadolinium atoms, is made in the form of collimator with channels oriented to the zone of radiation concentration from X-ray sources specified, the optical axes of the central channels of all collimators intersecting in a point, to which current results of measurements are referenced.

In this case, it is possible, for example, to use as a part of Roentgenooptical system quasi-point X-ray sources and collimators with channels focused on these sources, screen with an opening being situated between outlet of each X-ray source and inlet of the corresponding collimator.

In the case specified it is possible also to use as a part of Roentgenooptical system extended X-ray sources and collimators with channels diverging towards these sources.

In another particular case, X-ray sources comprising a part of Roentgenooptical system are quasi-point ones, each of means for X-ray radiation concentration in a zone comprising point, to which current results of measurements are referenced, is made in the form of X-ray half-lens transforming divergent radiation from corresponding source into the quasi-parallel one, and each of means for transportation of secondary radiation arising to detector sensitive to $K_\alpha$-radiation of gadolinium atoms—in the form of X-ray half-lens focusing this radiation on the detector. At that, optical axes of all X-ray half-lenses intersect in a point, to which current results of measurements are referenced.

In yet another particular case, X-ray sources comprising a part of Roentgenooptical system are quasi-point ones, each of means for X-ray radiation concentration in a zone comprising point, to which current results of measurements are referenced, is made in the form of X-ray half-lens transforming divergent radiation from corresponding source into the quasi-parallel one, and each of means for transportation of secondary radiation arising to detector sensitive to $K_\alpha$-radiation of gadolinium atoms—in the form of X-ray half-lens shaping quasi-parallel radiation and having a focus in a zone of X-ray radiation concentration. At that, optical axes of all X-ray half-lenses intersect in a point, to which current results of measurements are referenced.

In another particular case, X-ray sources comprising a part of Roentgenooptical system are quasi-point ones, each of means for X-ray radiation concentration in a zone comprising point, to which current results of measurements are referenced, is made in the form of X-ray half-lens transforming divergent radiation from corresponding source into the quasi-parallel one, and each of means for transportation of secondary radiation arising to detector sensitive to $K_\alpha$-radiation of gadolinium atoms—in the form of X-ray lens focusing this radiation on the detector sensitive to $K_\alpha$-radiation of gadolinium atoms and having second focus in zone of X-ray radiation concentration. In this case, optical axes of all X-ray half-lenses and lenses intersect in a point, to which current results of measurements are referenced.

It is possible also to make the device with X-ray sources comprising a part of Roentgenooptical system being quasi-point ones, each of means for X-ray radiation concentration in a zone comprising point, to which current results of measurements are referenced, being made in the form of X-ray half-lens transforming divergent radiation from corresponding source into the quasi-parallel one, and each of means for transportation of secondary radiation arising to detector sensitive to $K_\alpha$-radiation of gadolinium atoms—in the form of collimator with channels diverging towards corresponding detector. At that, optical axes of all X-ray lenses and half-lenses intersect in a point, to which current results of measurements are referenced.

Another one possible embodiment of the device proposed has a feature consisting in the X-ray sources comprising a part of Roentgenooptical system being quasi-point ones, each of means for X-ray radiation concentration in a zone comprising point, to which current results of measurements are referenced, being made in the form of X-ray half-lens transforming divergent radiation from corresponding source into the quasi-parallel one, and each of means for transportation of secondary radiation arising to detector sensitive to $K_\alpha$-radiation of gadolinium atoms—in the form of collimator with channels converging towards corresponding detector. At that, optical axes of all X-ray half-lenses and central channels of collimators intersect in a point, to which current results of measurements are referenced.

Another embodiment of the device is characterized in that the X-ray sources comprising a part of Roentgenooptical system are quasi-point ones, each of means for X-ray radiation concentration in a zone comprising point, to which current results of measurements are referenced, is made in the form of X-ray lens focusing divergent radiation from X-ray source, and each of means for transportation of secondary radiation arising to detector sensitive to $K_\alpha$-radiation of gadolinium atoms—in the form of X-ray lens focusing said radiation on corresponding detector. At that, optical axes of all X-ray lenses intersect in a point, to which current results of measurements are referenced.

The embodiment of the device proposed is also possible with X-ray sources comprising a part of Roentgenooptical system being quasi-point ones, each of means for X-ray radiation concentration in a zone comprising point, to which current results of measurements are referenced, being made in the form of X-ray lens focusing divergent radiation from X-ray source, and each of means for transportation of secondary radiation arising to detector sensitive to $K_\alpha$-radiation of gadolinium atoms—in the form of collimator with channels converging towards corresponding detector, the optical axes of all X-ray lenses and central channels of collimators intersecting in a point, to which current results of measurements are referenced.

The device proposed may also be made in such a way that X-ray sources comprising a part of Roentgenooptical system are quasi-point ones, and each of means for X-ray radiation concentration in a zone comprising point, to which current results of measurements are referenced, is made in the form of X-ray lens focusing divergent radiation from X-ray source. At that, each of means for transportation of secondary radiation arising to detector sensitive to $K_\alpha$-radiation of gadolinium atoms is made in the form of collimator with channels diverging towards corresponding detector, and optical axes of all X-ray lenses and central channels of collimators intersect in a point, to which current results of measurements are referenced.

In all the cases described, the device may be additionally provided with means for switching off or shielding of the detectors sensitive to $K_\alpha$-radiation of gadolinium atoms during periods of operation of X-ray sources having increased intensity.

BRIEF DESCRIPTION OF THE DRAWINGS

The inventions proposed are illustrated with drawings, in which.

EMBODIMENTS OF THE INVENTIONS

Figure 1:
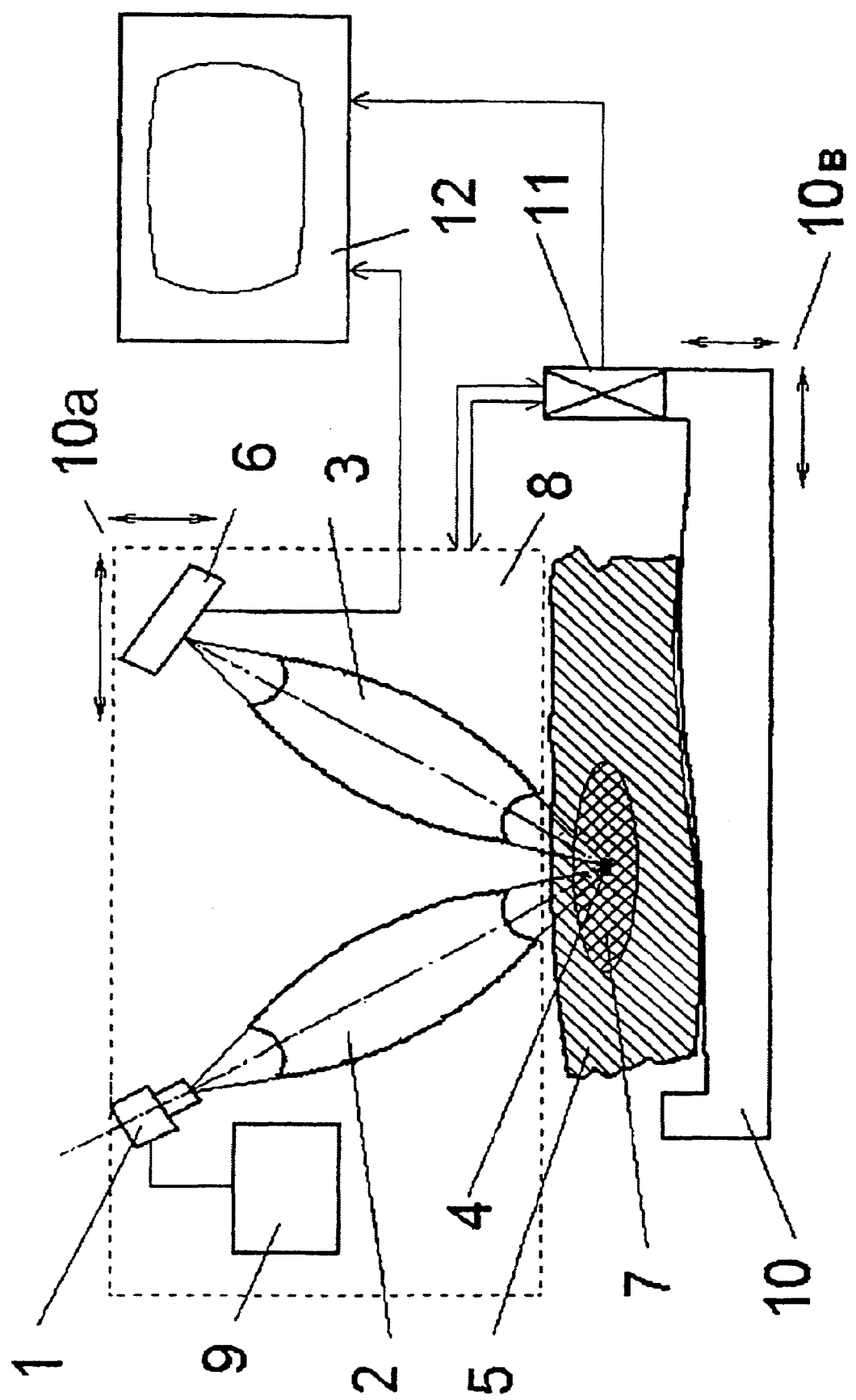
FIG. 1, which elucidates principles laid into basis of the methods proposed, shows schematically relative position and connection of major components of the device for implementation of the methods proposed.

The method proposed for determination of refined position of the malignant neoplasm is used as a stand-alone one if it is not followed with radiation treatment of the malignant neoplasm to accomplish damaging of its cells, or as a part of such treatment of the malignant neoplasm at the first stage of its realization. In both cases, this method as such is not a diagnostic or therapeutic one.

The method proposed of radiation treatment of the malignant neoplasm for damaging of its cells always comprises at the first stage of its realization a method proposed for position refinement of the malignant neoplasm.

Both methods abovementioned comprise method of gadolinium presence detection in tissues and organs of human body.

The device proposed is a common one for all methods.

The methods proposed are accomplished using the device proposed in a following way.

Divergent X-ray radiation from quasi-point source 1, generating radiation with energy corresponding to K-edge of gadolinium atoms absorption (FIG. 1), is focused with X-ray lens 2 in a predetermined point of part 7 of the patient body 5, comprising a malignant neoplasm, as found in the course of preceding diagnosis. The patient body is placed as required using means 10 for relative positioning of the patient body and Roentgenooptical system. Radiation with energy corresponding to the K-edge of gadolinium atoms absorption, focused in a point 4, excites secondary scattered radiation of biological tissues of patient 5 (coherent and incoherent Compton radiation, fluorescent radiation). In the case of the malignant neoplasm presence in the tissues of the part studied of patient body, $K_\alpha$-line of gadolinium will be prevalent in the secondary radiation due to gadolinium concentration. In the same point 4 focus is situated of the second X-ray lens 3. This lens is focusing scattered secondary radiation it captures on detector 6, sensitive to $K_\alpha$-radiation of gadolinium atoms, which converts it into electric signal fed to the input of means 12 for information processing and representation. Choice of position of common focus point 4 of lenses 2 and 3 is accomplished by way of relative displacement of the patient body 5 and Roentgenooptical system 8 using means 10 with the purpose of their relative positioning. The Roentgenooptical system 8 comprises X-ray source 1 made with possibility of radiation generation with energy corresponding to K-edge of gadolinium atoms absorption, and detector 6 sensitive to $K_\alpha$-radiation of gadolinium atoms, as well as means 9 for control of source 1 radiation intensity. Means 9 provides for simultaneous change of radiation intensity of all sources belonging to the Roentgenooptical system (FIG. 1, intended for illustration of basic principles of the inventions proposed, shows only one of them). Source 1 has also possibility of stepwise regulation of radiation intensity, for example, by way of anode current changes of X-ray tube. The additional possibility used together with that specified above or instead of it, may consist, for example, in temporary removal of a filter providing for selection of radiation having energy corresponding to K-edge of gadolinium atoms absorption. At that, due to broadening of radiation spectrum, its total intensity increases.

Possibility of radiation intensity changes and means 9 for its control are used in method of radiation treatment of the malignant neoplasm with the purpose of damaging its cells at the second stage of the method specified.

The X-ray lenses serving as means for X-ray radiation control (focusing of divergent radiation, shaping of quasi-parallel beam from divergent radiation, focusing of quasi-parallel beam, etc.) comprise an aggregate of curved channels for radiation transportation, in which radiation experiences multiple total external reflection (see, for example, V. A. Arkad'ev, A. I. Kolomijtsev, M. A. Kumakhov et al. Broadband X-ray optics with angular aperture. Uspekhi fizicheskikh nauk, 1989, vol.157, Issue 3, p.529-537 [4], where first such lens is described, and U.S. Pat. No. 5,744,813 (publ. Apr. 28, 1998) [5], with more up-to-date lens disclosed). Lens as a whole has a barrel-like shape (i.e., converging towards both end faces), if it is designed for divergent radiation focusing, or a half-barrel shape (i.e., converging towards one of the end faces), if it is designed for transformation of the divergent radiation into quasi-parallel one or for focusing such radiation. Two types of the lenses specified are commonly designated by terms "full lens" and "half-lens", correspondingly.

Two variants are possible of functioning and utilization of the device according to FIG. 1. In one of the variants, body of patient 5 remains fixed, and the Roentgenooptical system 8 (its possible movements are indicated in FIG. 1 with arrows 10a) is moving, with relative positioning of elements 1, 2, 3, and 6 remaining constant (and consequently, with coinciding focuses of lenses 1 and 3). In another variant, on the contrary, Roentgenooptical system 8 is stationary, and patient body 5 is moving (such movement is shown schematically in FIG. 1 with arrows 10b).

The device comprises also position indicator 11 responding to relative displacement of Roentgenooptical system 8 and patient body 5, connected to means 10 for relative positioning of patient body and Roentgenooptical system. Indicator 11 should be adjusted in such a way that its output signals would correspond to coordinates of the point, to which current results of measurements are referred relative to reference point chosen.

As the point specified, to which current results of measurements are referenced, in the particular case shown in FIG. 1, common focus point 4 is used of X-ray lenses 2 and 3, in which their optical axes intersect.

In other cases, when zone of radiation concentration is more diffused, such a point is also an intersection point of optical axes (or lines accepted provisionally as optical axes, such as axis of collimator's central channel) of radiation concentration means and means for transportation of secondary radiation arising to detectors. Using means 10 for relative positioning of patient body and Roentgenooptical system, position of the point specified should be ensured within boundaries of the part of patient body of interest, comprising (or presumably comprising) the malignant neoplasm.

Zone of radiation concentration is a region of larger or smaller dimensions, depending on the concentration means utilized, surrounding the point specified, to which current results of measurements are referenced (at the second stage of realization of radiation treatment method of the malignant neoplasm, concentration zone also surrounds intersection point of lines, which are optical axes of radiation concentration means and means for transportation of secondary radiation arising to detectors 6, although measurements at this stage may not be conducted). In the case shown in FIG. 1, concentration zone has minimal size.

Output signals of the indicator 11, similar to output signal of detector 6, are fed to inputs of means 12 for information processing and representation. As it was mentioned above, focus point 4 in the given case is a point, to which current results of measurements are referenced, and in which neighborhood (taking into account finite size of the focal zone of X-ray lens 2) radiation of source 1 is practically concentrated. Means 12 for information processing and representation provides for boundaries imaging of the malignant neoplasm 5 utilizing one or another algorithm of two-dimensional or three-dimensional image generation on display (see, for example, E. Lapshin. Graphics for IBM PC. Moscow, "Solon" publishers, 1995 [6]). In the simplest case when, for example, scanning (movement of concentration zone of X-ray radiation comprising a point 4, to which current results of measurements are referenced) is performed in any plane section of patient body 5, image may be produced synchronously on the display of means 12 with a prolonged afterglow; storage is also possible of a certain amount of results measured with subsequent periodic image displaying, etc. Possibilities of digital technology allow also to obtain image of density distribution in any plane section with other variants of scanning the volume of region containing the malignant neoplasm—not necessarily directly in the plane of interest. For this, it is sufficient to select from the results obtained (set of density values with corresponding coordinates values), relating to the volume containing the section required, the results corresponding to the section of patient body of interest, and to generate and display their two-dimensional image relative to coordinate axes situated in the section specified. Transformations necessary of this kind are performed by software means utilizing known methods similar to those described in [6].

All the inventions proposed are united in that they utilize nonuniformity of the introduced gadolinium distribution in body tissues having different nature, and its accumulation in tissues of the malignant neoplasms in concentrations exceeding by far those in the rest ("Prospects of Gadolinium Neutron Capture Therapy"; in book: Advances in Neutron Capture Therapy. Editors: B. Larsson, J. Crawford, R. Weinrech. Elsevier, 1997, part 2, pp.425-451 [7]). In the given work, taking into account the gadolinium property specified, possibility is discussed of its utilization for neutron capture and tumor exposure similar to method of boron-capturing therapy. In the inventions proposed, the property of preferential gadolinium concentration in the malignant neoplasm is used differently. The existence of this property is associated with the selective (by spectrum) action of radiation on tissues of the organs investigated and utilization as informative of secondary radiation excited by the primary one due to its action on the tissues rather than basic radiation (primary one, which is attenuated differently in different tissues). The techniques of the methods proposed and design of the device proposed provide for analysis with the detecting means exactly of secondary radiation, said analysis being also performed selectively due to utilization of detectors having maximum sensitivity in spectral region corresponding to $K_\alpha$-radiation of gadolinium atoms. As a result, detectors output signals corresponding to secondary radiation transmitted to their inlets from the region containing the malignant neoplasm exceed substantially the signals corresponding to other regions. Such difference in signal strength provides for reliable differentiation of region containing the malignant neoplasm in the course of scanning from surrounding tissues.

We would like to emphasize additionally that in the inventions proposed introduction of gadolinium-containing preparation into the body of patient is not directed to utilization of its radiopaque properties, because the method used is not associated with acquisition of shadow projections. Utilization of gadolinium secondary radiation quanta as informative ones comprises an important feature of the inventions proposed, as distinct from known methods and devices in which secondary radiation has interfering action. One of the consequences of said feature, essential in medical applications, lies in possibility of ensuring acceptable accuracy at lower irradiation doses of biological tissues.

Realization of methods of defined position determination and radiation exposure of the malignant neoplasm to damage its cells are preceded with investigations of the amount required of gadolinium-containing preparation and its period of accumulation in organs and tissues subject to irradiation. In the course of these investigation the method proposed is realized for detection of gadolinium presence. The amount required of the preparation and the accumulation time mentioned are determined due to this for the specific means available and with account of individual features of particular patient, kind of organs and tissues affected, as well as the preparation used and method of its introduction.

As gadolinium-containing preparations, in particular, four commercial radiopaque agents may be used, mentioned in Russian Federation patent No. 2,150,961, which found application in clinical practice. All of them are gadolinium complexes with organic ligands. Such preparations include Magnevist, produced by Schering AG (Germany) (aqueous solution of gadopentate dimeglumine salt), Omniscan, produced by Sanofi Winthrop (Norway), N.Y., Nycomed (aqueous solution of gadolinium complex with diethylenetriaminopentaacetic acid diamine), DOTAREM™-Laboratoire Gurbet, Aulnay Sous Bois (France) (gadoterate maglumine salt), and Pro Hance, Gadoteridol, joint production of USA (Bristol-Myers Squibb) and Italy (Bracco). The most widely used preparations are those on base of diethylenetriamino-pentaacetic acid (DTPA), in particular, Magnevist. May be used also a preparation proposed in patent specified, which is an improvement of Magnevist preparation. One more gadolinium-containing preparation has been proposed in Russian Federation patent No. 2,081,881. A whole series of other preparations has been proposed in U.S. Pat. Nos. 6,040,432; 5,965,132, etc. Depending on the organ affected, preparation forms may be used suitable for parenteral or enteral introduction, for example, by injection or infusion, or the preparation may be introduced directly into body cavity having an outward outlet, for example, gastrointestinal tract and urinary bladder.

Let us make an estimate of irradiation doze of patient in the method proposed.

According to [7], density of gadolinium atoms in the malignant neoplasm may be on the level of one milligram of gadolinium per gram of biological tissue.

Let's consider a case of a malignant neoplasm having size of 1 cm$^3$.

Coefficient of X-ray radiation absorption with gadolinium atoms near K-edge of absorption, $\mu_{max}$150 cm$^{-1}$; absorbance discontinuity jump, S, is determined as $\mu_{max}/\mu_{min}$ ratio; in our case, $\mu_{min}$=25 cm$^{-1}$, i.e. S≈6.

Fraction of photons absorbed taking part in the process of gadolinium K-series excitement, is proportional to coefficient $$1-1/S=1-1/S\approx 1-0.84.$$

Fluorescence efficiency, $\omega$, for gadolinium equals to:

$$\omega\approx 0.95.$$

Number of fluorescent photons, $N_F$, emitted with unit surface, equals to:

$$N_F=N_0\mu_{max}S\Delta x(1-1/S)\omega, \quad (1)$$

where $N_0$ denotes initial number of photons hitting the volume specified;

$\Delta x$ is a characteristic dimension (in our case, $\Delta x$=1 cm).

Let's take gadolinium content in 1 cm$^3$ equal to 1 milligram. In this case, product of $\mu_{max}$ S equals to $2\cdot 10^{-2}$ cm$^{-1}$.

Consequently, $N_F=N_0\cdot 2\cdot 10^{-2}\cdot 0.84\cdot 0.95=N_0\cdot 1.6\cdot 10^{-2}$.

For the purpose of further estimate, let us consider ca.5% of photons emitted being registered by detector with probability of 1. Let's consider that we will obtain sufficiently accurate information on the malignant neoplasm localization if we register 10$^3$ fluorescent photons. This ensures reliability of ab.97%.

Hence, number of initial photons, $N_0$, required for registration of 10$^4$ photons by the detector:

$$N_0=10^3:(5\cdot 10^{-2}\cdot 1.6\cdot 10^{-2})=1.2\cdot 10^6.$$

To estimate the dose, we need to take into account losses of initial beam intensity on passing through biological tissue and losses of gadolinium K$_\alpha$-radiation on the way from the volume considered to the detector. Let us consider, for example, a case of the malignant neoplasm investigated being situated at a depth of 5 cm.

In this case, if initial beam energy equals to 50 keV, said losses will be determined by formula:

$$I=I_0\cdot e^{-\eta x},$$

where $I_0$ denotes initial intensity of beam hitting the surface. For radiation with energy of 50 keV absorption coefficient in tissues $\eta\approx 0.2$ cm$^{-1}$, i.e. the intensity of incident radiation is reduced over the length of 5 cm by a factor of e≈2.71. Radiation of K$_\alpha$-line is a little less than 50 keV, hence, we can assume that over the path photons travel their intensity is reduced by a factor of 4. Accordingly, total intensity decreases by 2.7·4≈10 times. It means that the required amount of initial photons $N_0$ should be increased by 10 times, i.e. $N_0$=1.2·10$^7$ photons. If we suppose that all these photons are absorbed in a cylindrical layer of 1 cm diameter and 5 cm length, then estimate radiation dose amounts to:

$$b\approx 1.2\cdot 10^7\cdot 5\cdot 10^4 \, eV:5 \, \text{gram}=1.2\cdot 10^{-5} \, \text{Roentgen}.$$

This is radiation dose averaged over 5 cm depth. On the surface, dose will be a little higher than that averaged estimate due to exponential nature of absorption. Nevertheless, this dose is approximately 10$^3$ times below that of tomographic diagnostics, having an order of 0.01 R (Handbook on X-ray engineering. V. V. Klyuev, Ed. Part 2, p.347. Moscow, Mashinostroeniye Publishing House, 1980 [8]).

The dose may be additionally reduced by several times if irradiation is performed with several sources, whose beams reach concentration zone over different paths, not summing up in patient body.

Therefore, the most expedient embodiments of the methods and device proposed are those utilizing several spatially separated X-ray radiation sources and detectors with corresponding number of means for radiation concentration and transportation of secondary radiation to the detectors (lenses, half-lenses, collimators). On the one hand, it allows to achieve more efficient radiation concentration (in the case of single means for concentration this is possible only with utilization of X-ray lens, as shown in FIG. 1) and to increase signal/noise ratio at detectors output. On the other hand, it makes it possible to achieve more distributed action on the irradiated part of patient body and to avoid overdosing of parts and organs not requiring examination. Utilization of several detectors with simple averaging (or more complex processing of output signals in means 12 for information processing and representation, for example, by weight averaging or processing accounting for density correlation in closely situated points) and subsequent comparison of averaging result with registration threshold for the secondary radiation created with gadolinium atoms allows, other things being equal, to use X-ray sources of minor power without loss of accuracy. Besides, the averaging diminish effect of other factors lowering the accuracy (for example, nonuniform absorption of the sources radiation on its way to different points in which density is measured, and of secondary radiation on the way from those points to inlets of means for secondary radiation transportation to the detectors).

Below (FIG. 2-FIG. 11) exactly such variants are discussed.

Figure 2:
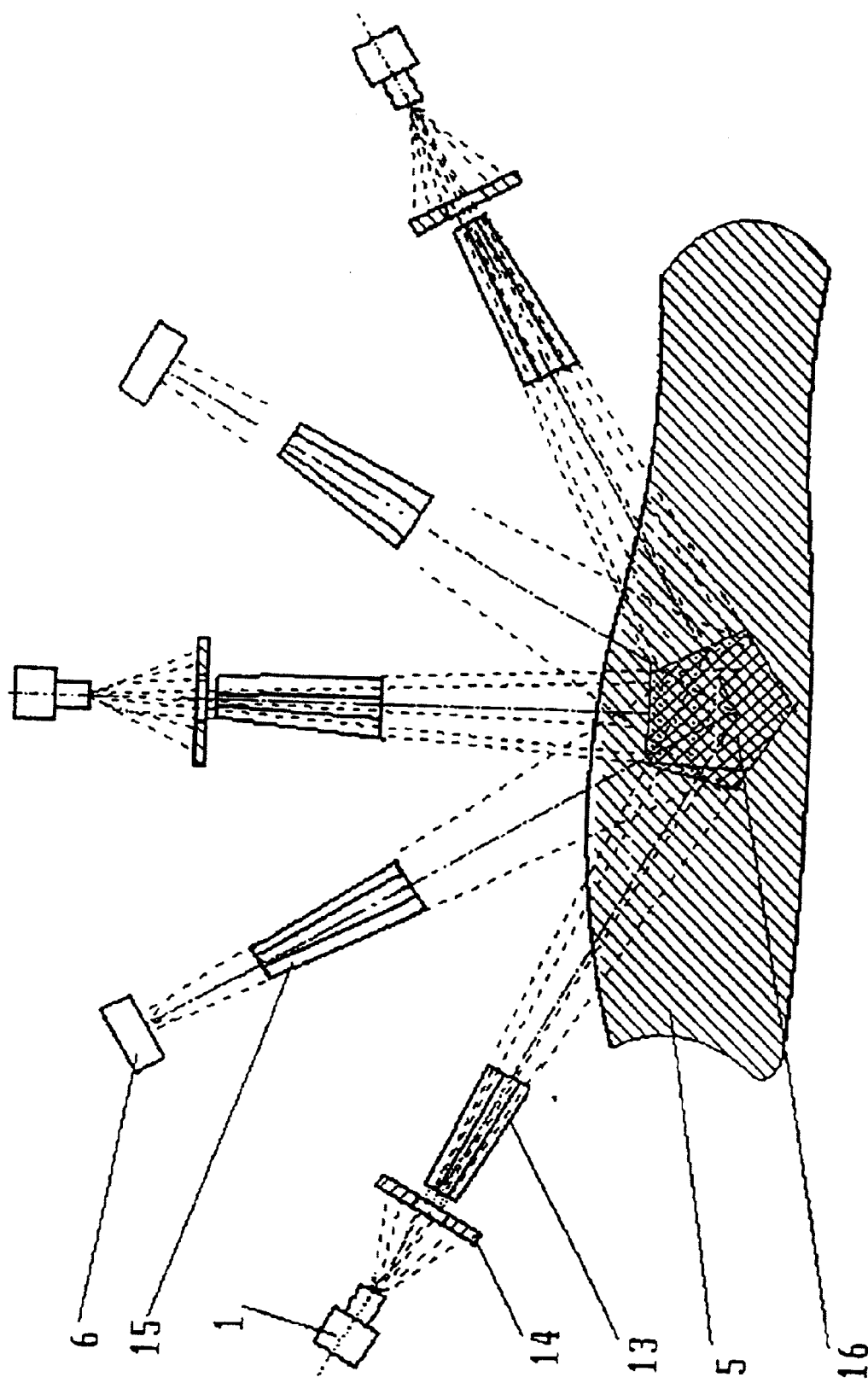
FIGS. 2 and 3 show specific embodiments of methods and design of devices utilizing collimators for concentration of X-ray radiation and transportation of secondary radiation to the detectors.
Figure 3:
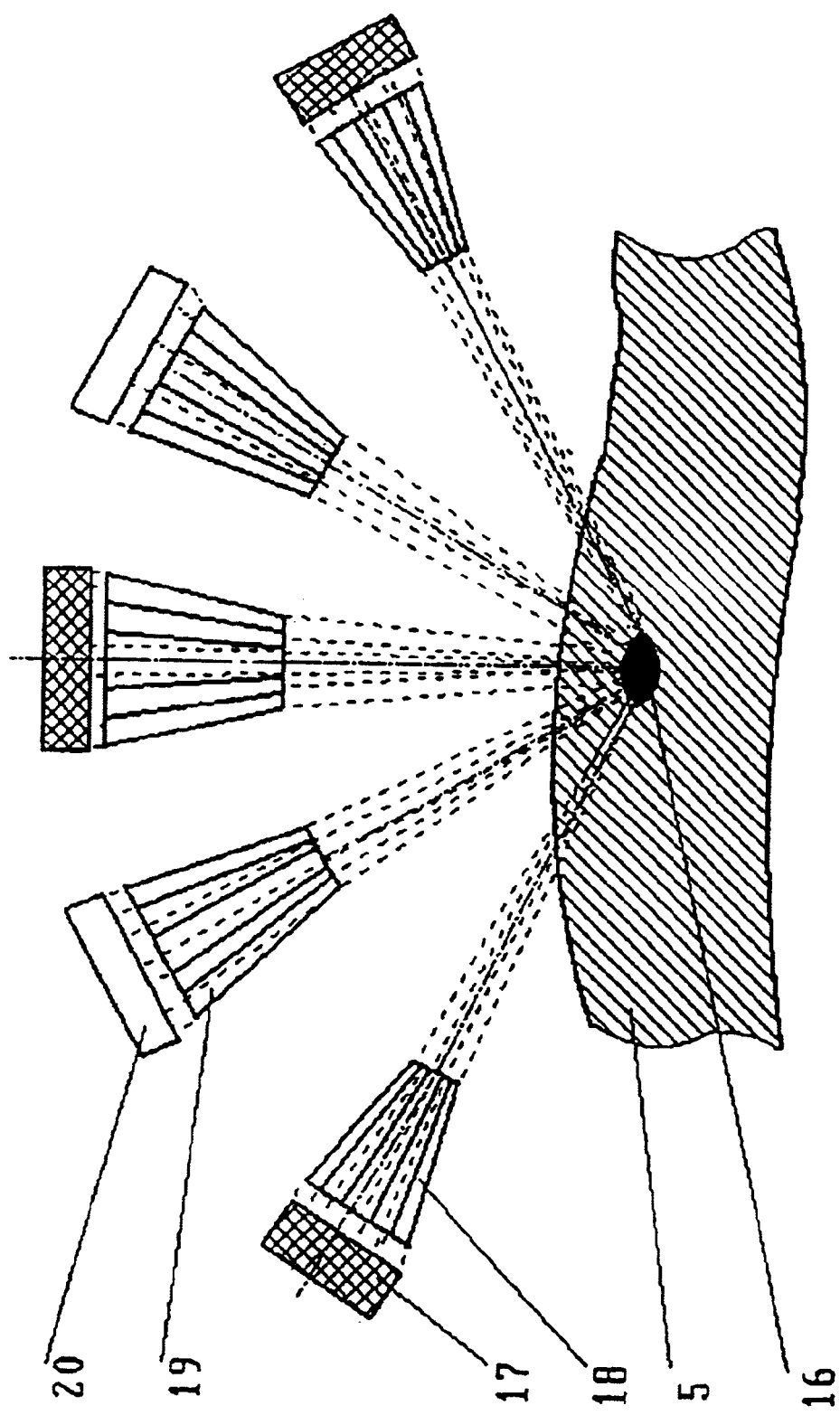

The embodiments most simple for technical realization are shown in FIG. 2 and FIG. 3.

In the design of FIG. 2, quasi-point X-ray sources 1 and collimators 13 with channels diverging (expanding) in the direction of radiation propagation are utilized for its concentration in zone 16. Between sources 1 and collimators 13 shields 14 with openings are installed for radiation transmission to the inlets of collimators and prevention of direct (in bypass of the collimators) exposure of the object. Secondary radiation is transported to detectors 6 by of collimators 15 with channels converging (tapering) in the direction of radiation propagation, i.e. towards detectors 6, and may have a focus on their sensitive surface. As detectors 6, for example, semiconductor detectors may be used having small entrance aperture.

In FIG. 3, collimators have orientation opposite to that shown in FIG. 2. For a full usage of entrance aperture of collimators 18 concentrating radiation in zone 16, it is expedient to employ extended X-ray sources 17. By similar reason, it is expedient to use detectors 20 having large entrance aperture (for example, those of scintillation type).

Figure 4:
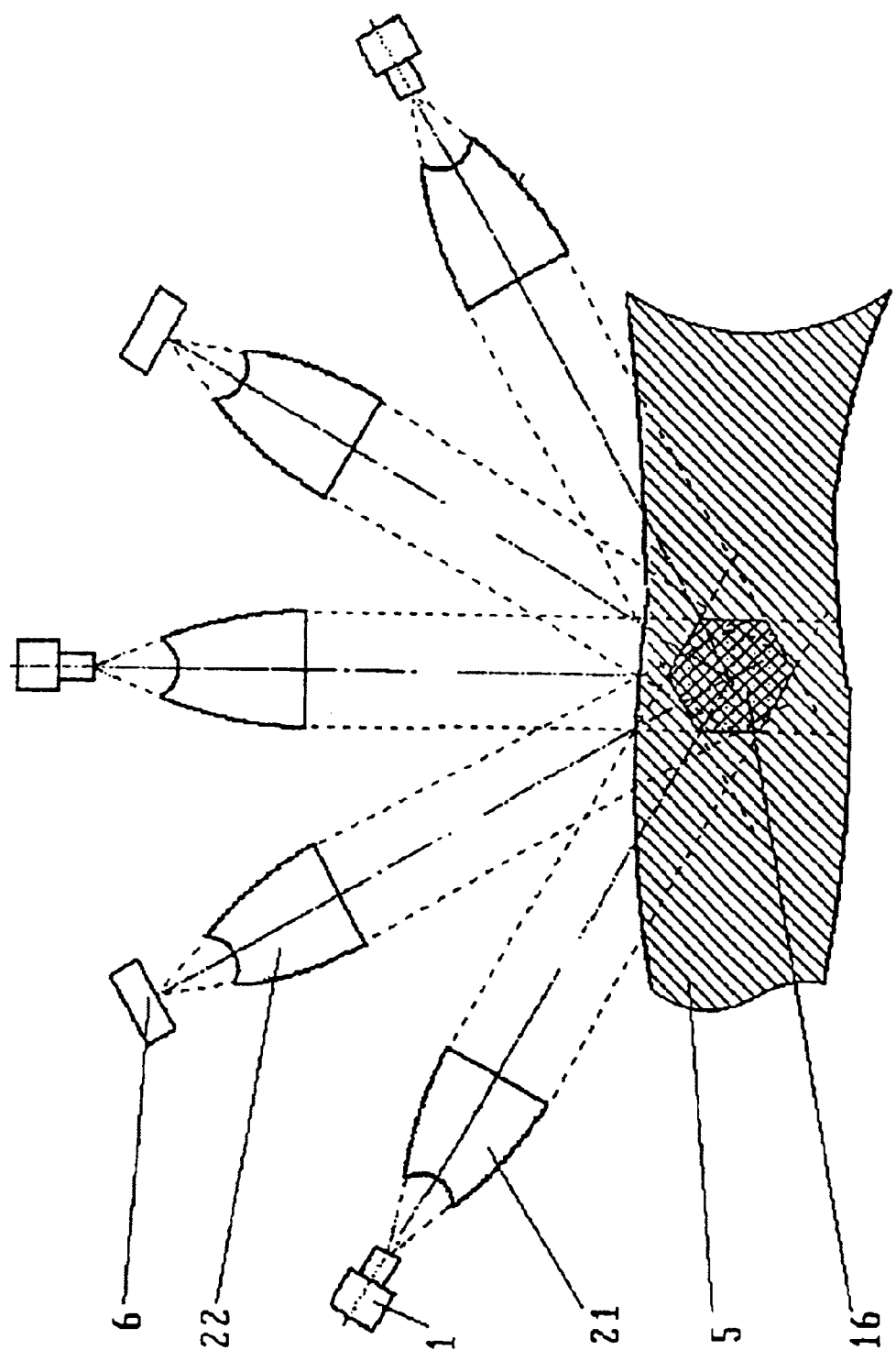
FIGS. 4 and 5 show the same as above, with utilization of X-ray half-lenses.

In FIG. 4, means for concentration of quasi-point sources 1 radiation and means for secondary radiation transportation are made in the form of X-ray half-lenses 21, 22, correspondingly. At that, half-lenses 22 focus scattered secondary radiation on the detectors 6.

Figure 5:
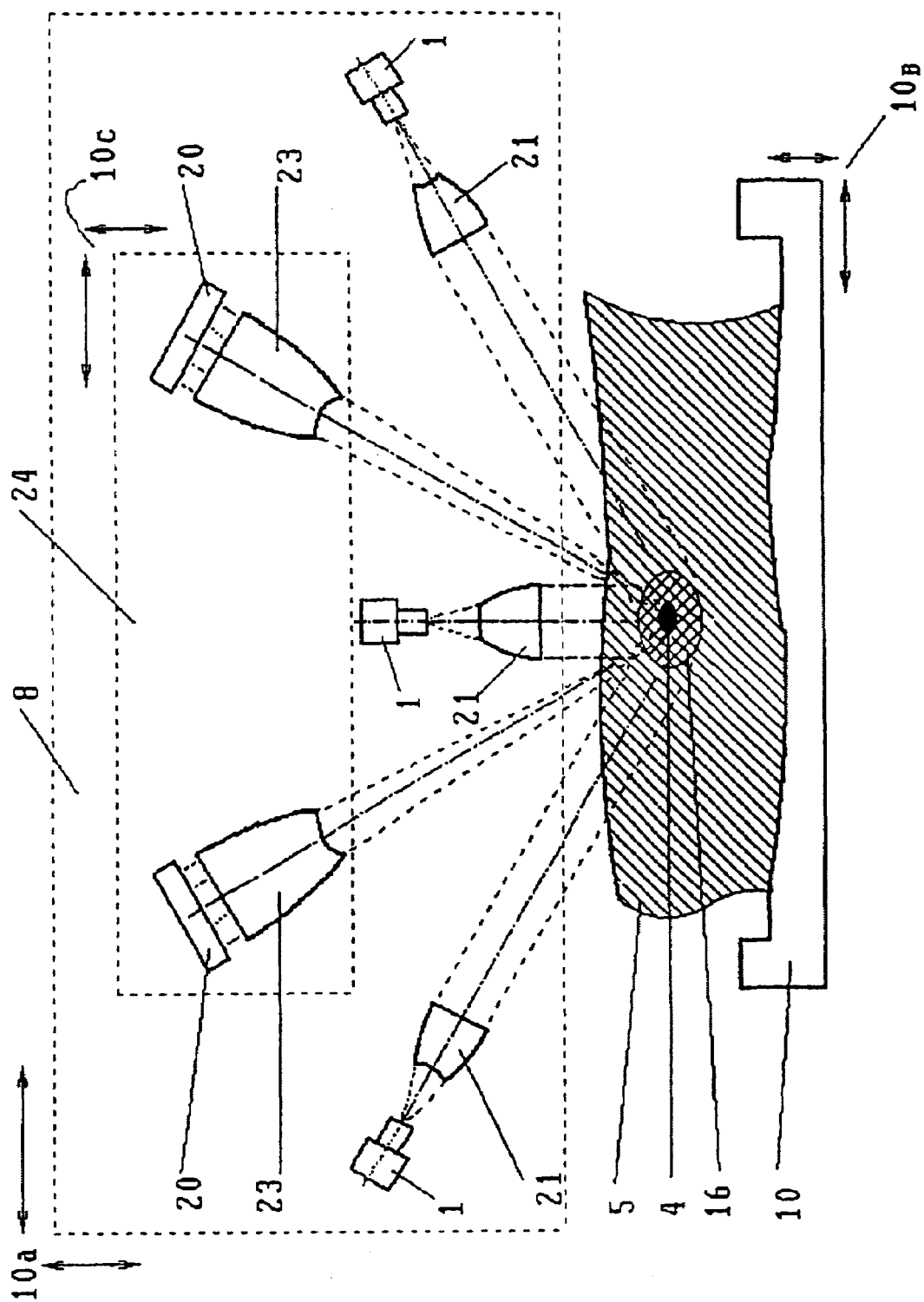

In FIG. 5, means for concentration of quasi-point sources 1 radiation and means for secondary radiation transportation are made in the form of X-ray half-lenses 21, 23, correspondingly. At that, half-lenses 23 transform scattered secondary radiation into the quasi-parallel one and direct it to the detectors 20 having large entrance aperture.

Figure 6:
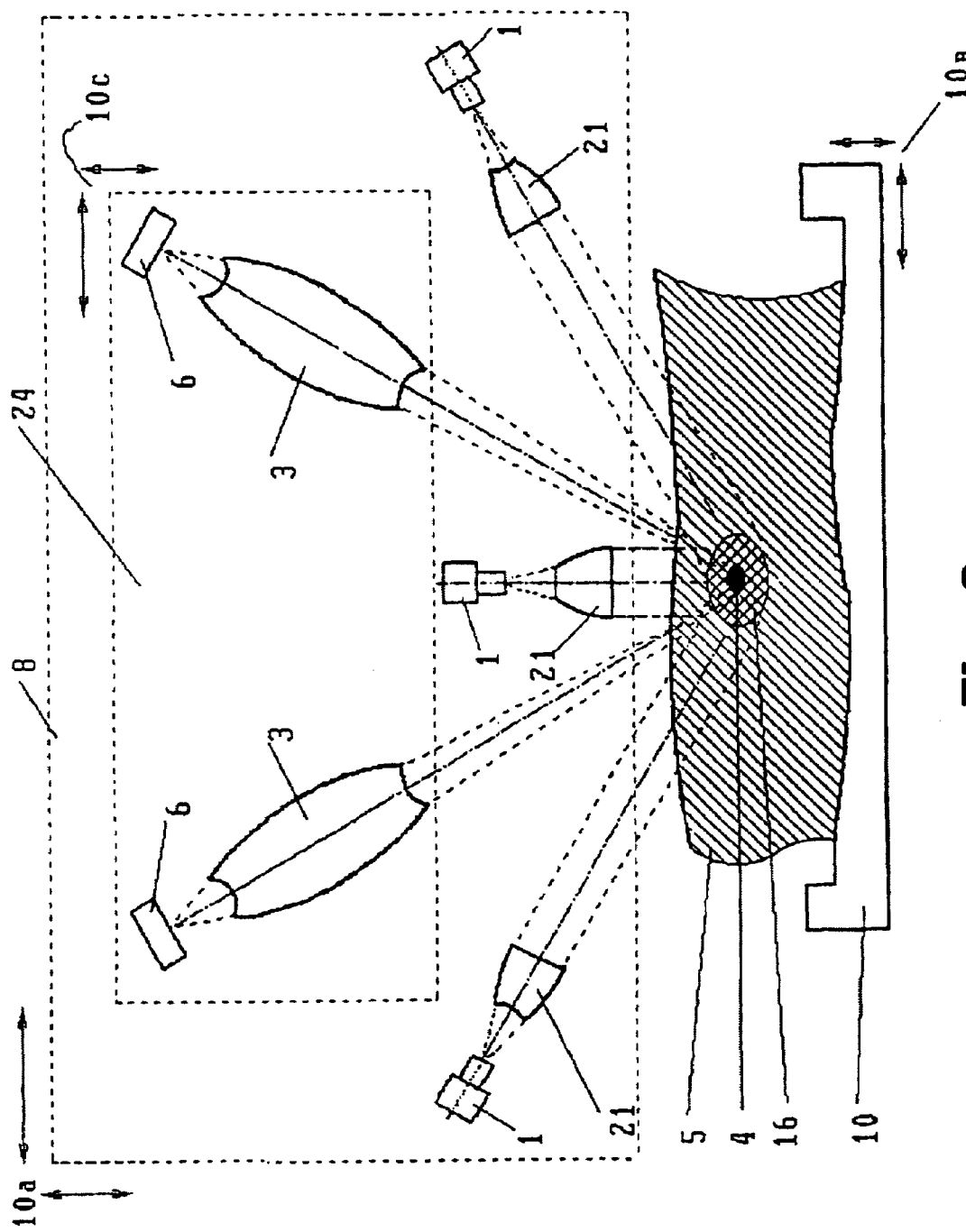
FIG. 6 shows the same as above, with utilization of X-ray half-lenses for concentration of X-ray radiation, and "full" X-ray lenses—for transportation of secondary radiation to detectors.

In FIG. 6, composite variant is demonstrated: means for concentration of quasi-point sources 1 radiation are made in the form of X-ray half-lenses 21, directing parallel beams to zone 16, and means for secondary radiation transportation to the detectors 6—in the form of "full" X-ray lenses.

FIG. 5 and FIG. 6 simultaneously illustrate the embodiments of the methods proposed, in which scanning of the region under examination with a zone of concentration of radiation formed by the sources is combined with more accurate scanning within boundaries of zone specified with field of view of secondary radiation detector(s) having smaller dimensions. In this case, zone 16 of concentration of radiation from three sources 1 is formed with three half-lenses 21 transforming divergent radiation from these sources into quasi-parallel one. Transportation of secondary radiation to two detectors 20 (FIG. 5) and 6 (FIG. 6) is performed by two half-lenses 23 and two full lenses 3, correspondingly, which have common focus spot 4. Scanning is accomplished in such a way that at first, position of concentration zone 16 is changed by relative displacement of means 10 for patient 5 positioning and Roentgenooptical system 8. Then, scanning is performed within boundaries of region occupied by concentration zone 16 in its current position shown in FIG. 5 and FIG. 6, with a common field of view of detectors 20 (FIG. 5) and 6 (FIG. 6), which is a focus spot 4 having smaller dimensions in comparison with zone specified. These dimensions determine the final spatial accuracy of position fixation of the malignant locus. To realize these embodiments, means for secondary radiation transportation (in the given case—half-lenses 23 and full lenses 3) to detectors 20 and 6 and the detectors themselves, which are elements of Roentgenooptical system 8, are installed in said system with possibility of joint displacement relative to other elements of said system (sources 1 and half-lenses 21). In view of the above, said means for secondary radiation transportation in FIG. 5 and FIG. 6 are combined in subsystem 24, with possibilities of movement as an integral unit shown by arrows 10c.

Figure 7:
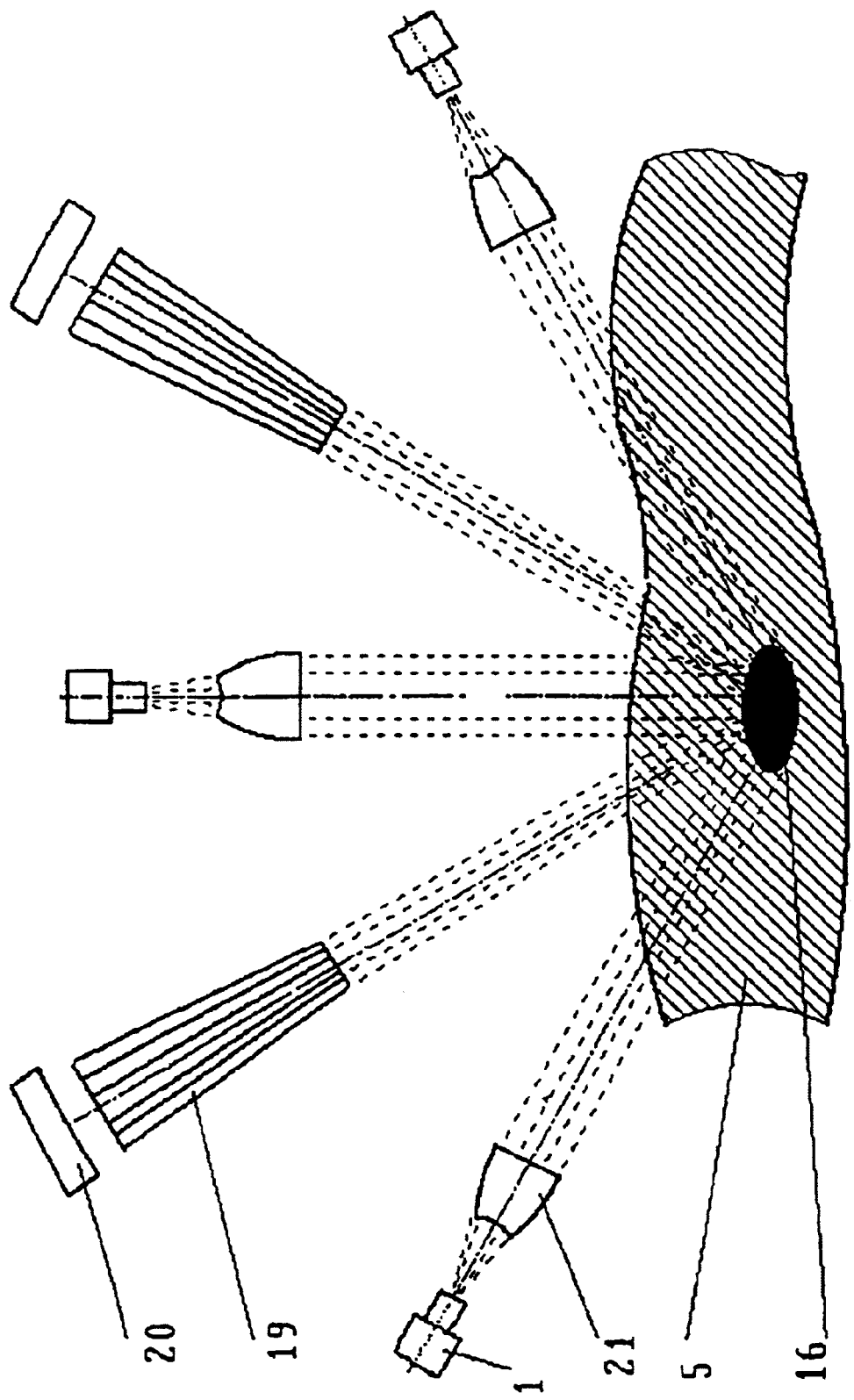
FIGS. 7 and 8 show the same as above, with utilization of X-ray half-lenses for concentration of X-ray radiation, and collimators—for transportation of secondary radiation to the detectors.
Figure 8:
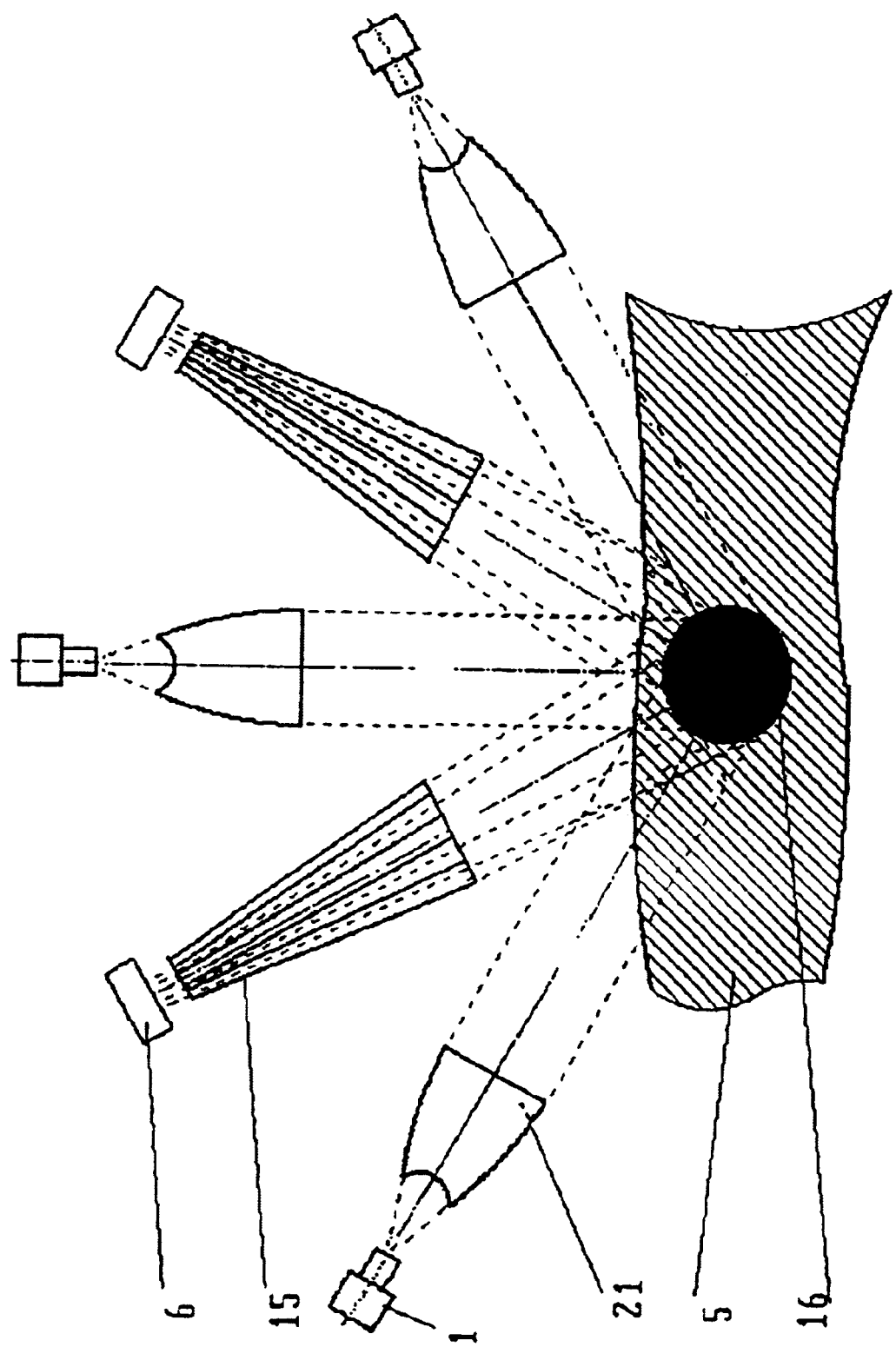

In FIGS. 7 and 8, other combinations are shown, which differ from the previous two in that the means for secondary radiation transportation to the detectors are made in the form of collimators.

In FIG. 7, collimators 19 have channels diverging towards detectors 6, while the latter have large entrance aperture.

In FIG. 8, vice versa, collimators 15 have channels converging towards detectors 6, while the latter have small entrance aperture.

Figure 9:
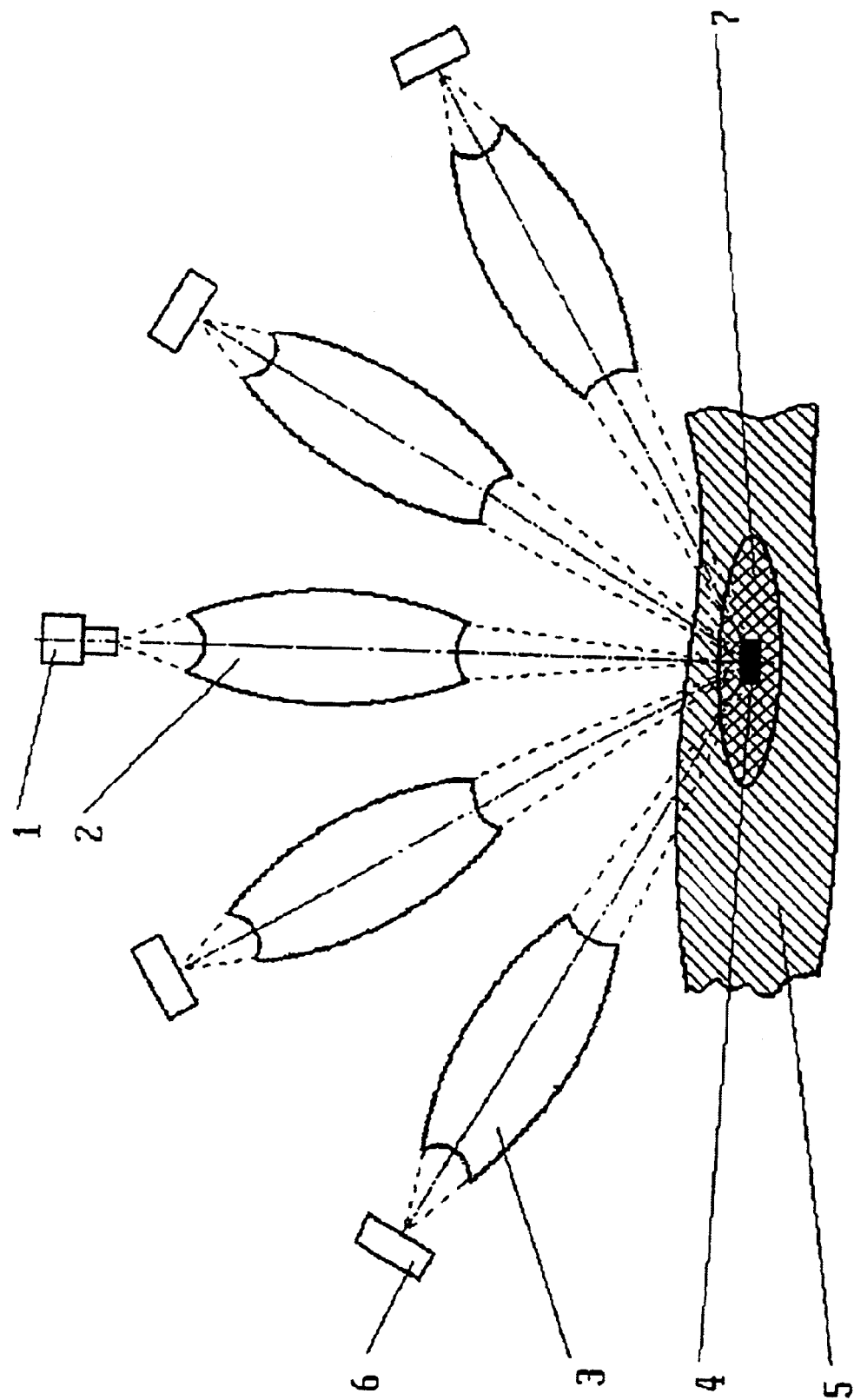
FIG. 9 shows the same as above, with utilization of X-ray lenses for concentration of X-ray radiation and transportation of secondary radiation to the detectors.

FIG. 9 shows the most efficient in respect to accuracy and resolving capacity variant, in which means for concentration of radiation from quasi-point sources 1 and means for secondary radiation transportation to detectors 6 are made in the form of "full" lenses 2 and 3, correspondingly (cf. this embodiment with that shown in FIG. 1).

Figure 10:
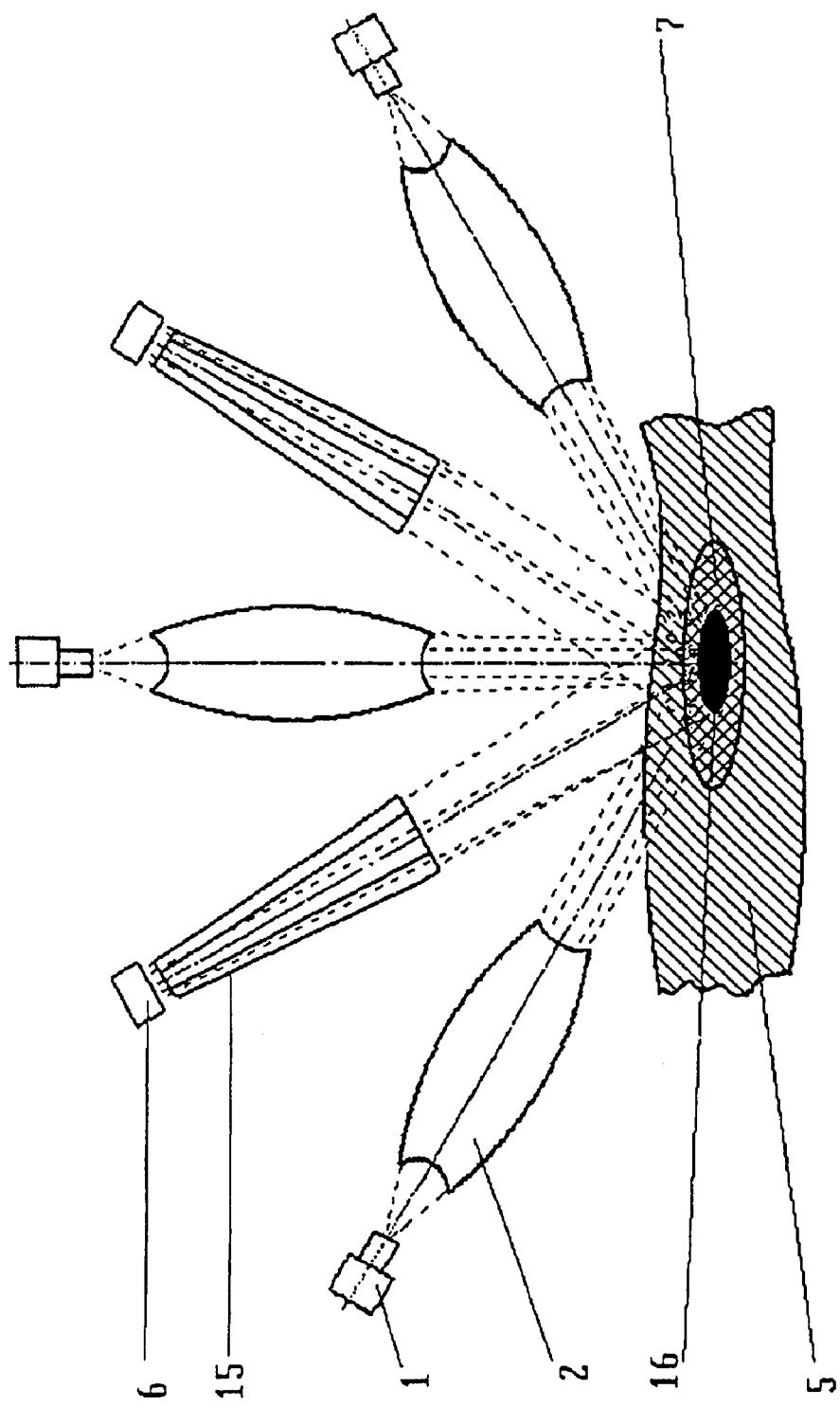
FIGS. 10 and 11 show the same as above, with utilization of X-ray lenses for concentration of X-ray radiation and collimators—for transportation of secondary radiation to the detectors.
Figure 11:
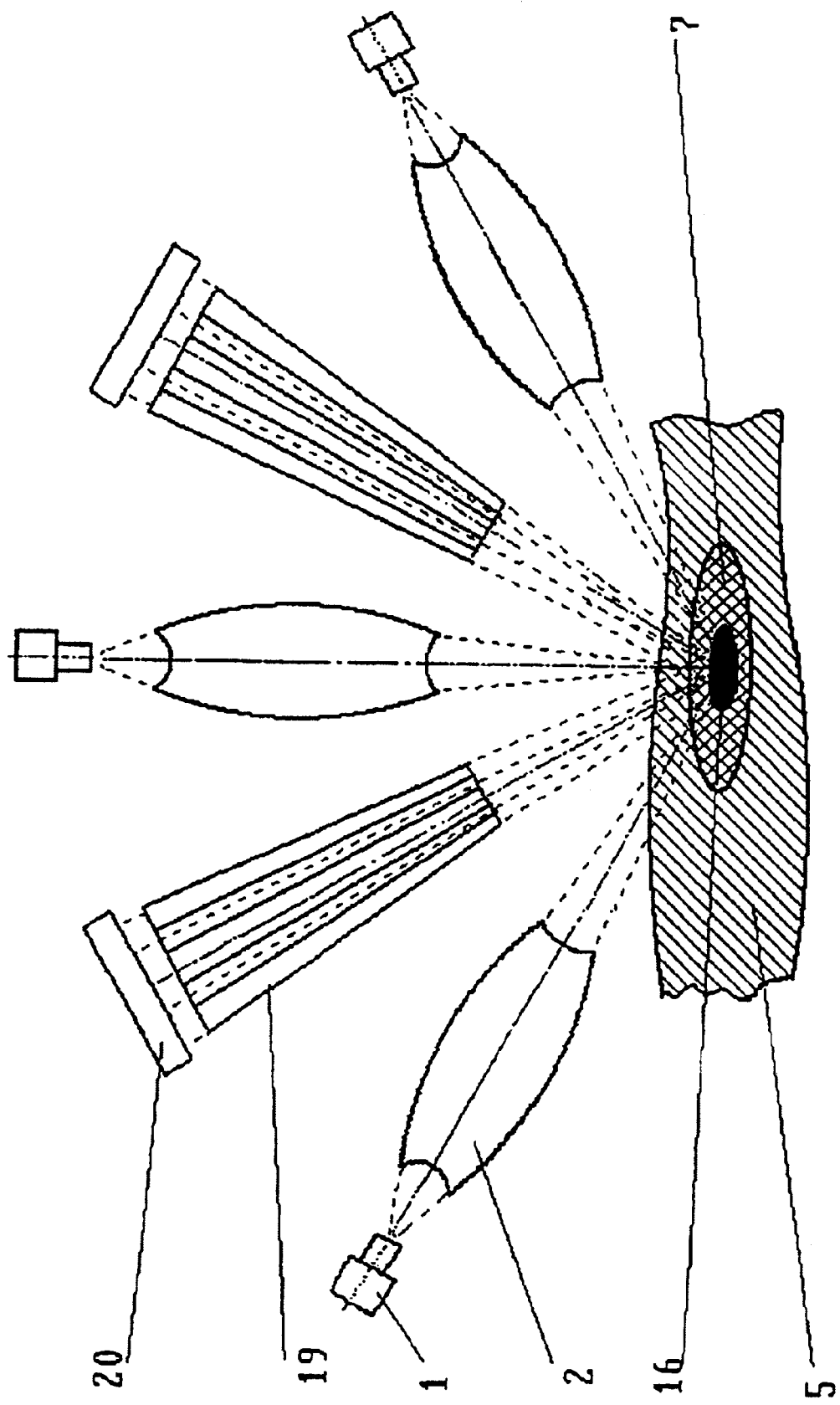

In FIGS. 10 and 11, two more composite variants are shown. They are united in that the "full" X-ray lenses 2 are used as means for concentration of radiation from quasi-point sources 1.

FIG. 10 shows utilization of collimators 15 converging towards detectors as means for secondary radiation transportation to the detectors 6 having small aperture.

FIG. 11 shows utilization of collimators 19 diverging towards detectors as means for secondary radiation transportation to the detectors 20 having large aperture.

In all the particular cases of the device embodiment, relative positioning of roentgenooptical system 8 elements should exclude possibility of radiation access to the inlets of detectors (6,20) directly from sources (1, 17) or on passing through patient (5) body, because useful information is carried by secondary radiation arising in zone of concentration. For that, no detectors (and means for secondary radiation transportation to the same) should be situated on the continuation of optical axis of any means for concentration of radiation from sources in concentration zone comprising intersection region of X-ray radiation beams formed with these means.

The method proposed for determination of the malignant neoplasm location and operation of the device proposed in realization of said method are concluded with fixation of coordinates combinations of the points identified as belonging to the malignant neoplasm (for example, by storage of corresponding groups of numerical codes in the means for information processing and representation). Identification is performed, for example, with the known method [3], by comparison of the images obtained in the process of method realization with those obtained in the result of previous diagnostics. At that, identified images of structural elements may be marked by operator taking part in the method realization on the display of means for information processing and representation using pointing device traditional for computing means, such as a "mouse".

If a decision is made on performing radiation exposure of the malignant neoplasm with the purpose of damaging its cells, then irradiation program is generated before further use of the device in the form of a set of X-ray radiation doses, which should be supplied to different parts of the malignant neoplasm represented with fixed sets of the points coordinates. Program of irradiation is generated using techniques described, for example, in [1], taking into account peculiarities of organ affected with the malignant neoplasm and other factors.

The program of irradiation is realized in the process of scanning of spatial region occupied by the malignant neoplasm. At that, the same means are used to concentrate X-ray radiation (lenses 2, 21; and collimators 13, 18) as in the first stage, i.e. in realization of method of refinement of the malignant neoplasm position. At that, with the help of means 9 for joint control of radiation intensity of X-ray sources, the latter are switched on in each of discrete positions of radiation concentration zone for a period of time, proportional to the dose required at elevated intensity level (provided for, for example, by increase in anode current of X-ray tubes), sufficient for radiation damage of the malignant neoplasm cells. In a particular case, at small dimensions of the malignant neoplasm, the irradiation may be performed at a single position of zone of X-ray radiation concentration, i.e. without scanning. By utilization of full lenses for radiation concentration, it is possible to perform radiation exposure of microtumors (for example, those of eye).

To prevent possible failure of detectors, they may be switched off or shielded mechanically for a period of operation of X-ray sources at elevated intensity level (means specified are not shown in the figures).

Utilization of one and the same means for radiation concentration in the course of position refinement of the malignant neoplasm (at the first stage of radiation treatment of the malignant neoplasm with the purpose of damaging its cells) and during realization of irradiation program (at the second stage) in combination with small spacing in time between those stages provide for minimization of "aiming" errors of radiation beams. Irradiation is performed at the same positions of radiation concentration zone as in the stage of position determination of the malignant neoplasm, because roentgenooptical system is placed in the positions relative to patient body coinciding with those fixed during scanning as belonging to the malignant neoplasm. The accuracy of roentgenooptical system readjustment relative to patient body in a position corresponding to coordinates fixed at identification, may be enhanced by utilization of advanced means for relative positioning, for example, similar to those described in [2].

Utilization of that or another arrangement of realization of the methods proposed and design variants of the device is determined both by possibility of employing such efficient means for radiation concentration and transportation, which are X-ray lenses or half-lenses, and the resolving capacity required. The latter factor affects also choice of parameters of lenses and half-lenses (such as focus spot dimensions, length of focal zone in the direction of optical axis of the lens, etc.). At that, it is taken into account that realization of very high resolving power on utilization of "full" lenses (of the order of fractions of millimeter and higher) is connected with increase in time required for scanning the region containing the malignant neoplasm. Other circumstances are also taken into account, such as availability of X-ray sources having suitable power and dimensions, etc.

The availability of the described and numerous other variants of realization of the method proposed and designs of the device proposed offers wide possibilities for the design of the means satisfying specific requirements presented.

INDUSTRIAL APPLICABILITY

The methods proposed for determination of refined position of the malignant neoplasm and radiation treatment of said neoplasm with the purpose of damaging its cells and the device for their realization are employed in conditions of diagnostics of the malignant neoplasm being carried out previously and the need exists in refined data acquisition on its position, shape, dimensions, and possibly, also in performing radiation treatment, if corresponding decision has been made earlier or is made in the course of acquisition of refined data specified.

SOURCES OF INFORMATION

1. Radiation therapy of malignant tumors. Physician's handbook. Prof. E. S. Kiseleva, Ed., Moscow, "Meditsina" publishing house, 1996 (in Russian).
2. U.S. Pat. No. 5,983,424, publ. 16 Nov. 1999.
3. U.S. Pat. No. 5,207,223, publ. 4 May 1993.
4. V. A. Arkad'ev, A. I. Kolomijtsev, M. A. Kumakhov et al. Broadband X-ray optics with angular aperture. Uspekhi fizicheskikh nauk (Progress in Physical Sciences), 1989, vol.157, Issue 3, p.529-537 (in Russian).
5. U.S. Pat. No. 5,744,813, publ. 28 Apr. 1998.
6. E. Laphin. Graphics for IBM PC. Moscow, "Solon" publishers, 1995 (in Russian).
7. Prospects of Gadolinium Neutron Capture Therapy (in book: Advances in Neutron Capture Therapy. Editors: B. Larsson, J. Crawford, R. Weinrech. Elsevier, 1997, part 2, pp.425-451).
8. Handbook on X-ray engineering. V. V. Klyuev, Ed. Part 2, p.347. Moscow, Mashinostroeniye Publishing House, 1980 (in Russian).

The invention claimed is:

1. Method of radiation treatment of the malignant neoplasm with the purpose of damaging its cells utilizing X-ray radiation beams, comprising the steps of:
   introducing gadolinium-containing substance into patient body;
   emitting X-ray radiation with energy corresponding to K-edge of gadolinium atoms absorption;
   using a concentration element, concentrating the X-ray radiation in a concentration zone within the part of patient body containing the malignant neoplasm;
   transporting secondary radiation arising in said zone to at least one detector having maximum sensitivity in a spectral region corresponding to $K_\alpha$-radiation of gadolinium atoms, for providing selective secondary radiation detection;
   scanning the part of patient body containing the malignant neoplasm by relative displacement of the concentration zone and the patient body;
   performing registration of the secondary radiation excited in the concentration zone using said at least one detector;
   performing registration of parameters, which characterize spatial position of the concentration zone and a field of vision of said at least one detector having a signal detected at the output;
   identifying each of regions common for the concentration zone and the field of vision of said at least one detector having a signal detected at the output, as containing cells of the malignant neoplasm;
   determining position of the malignant neoplasm based on the identified regions; and
   executing an irradiation program developed as a set of X-ray radiation doses that should be supplied to various points of the malignant neoplasm, by placing the concentration zone in positions corresponding to the determined position of the malignant neoplasm, using the concentration element utilized for detecting position of the malignant neoplasm,
   the irradiation program being executed by controlling duration of irradiation at an increased intensity level of X-ray radiation compared to X-ray radiation intensity provided for detecting position of the malignant neoplasm.

2. Method according to claim 1, wherein the concentration element include at least one collimator, and transportation of the secondary radiation to said at least one detector is performed using at least one further collimator, all the collimators being oriented in such a way that optical axes of their central channels would intersect in a single point.

3. Method according to claim 1, wherein the concentration of X-ray radiation in the concentration zone is accomplished with one or more X-ray half-lenses transforming divergent radiation into the quasi-parallel one, and transportation of the secondary radiation to said detector is performed using one or more X-ray half-lenses focusing secondary radiation on said detector or shaping a quasi-parallel radiation, all the X-ray half-lenses being oriented in such a way that their optical axes would intersect in a single point.

4. Method according to claim 1, characterized in that the concentration of X-ray radiation in the concentration zone is accomplished with one or more of X-ray half-lenses transforming divergent radiation from corresponding number of spatially separated X-ray sources into the quasi-parallel one, and transportation of the secondary radiation to said detector is performed using one or more X-ray lenses focusing secondary radiation on said detector, all the X-ray lenses and half-lenses being oriented in such a way that their optical axes would intersect in a single point.

5. Method according to claim 1, wherein the concentration of X-ray radiation in the concentration zone is accomplished with several X-ray half-lenses transforming divergent radiation from corresponding number of spatially separated sources into the quasi-parallel one, and transportation of the secondary radiation to said detector is performed using one or more collimators, X-ray half-lenses and collimators being oriented in such a way that optical axes of all X-ray half-lenses and central channels of all collimators would intersect in a single point.

6. Method according to claim 1, wherein the concentration of X-ray radiation in the concentration zone is accomplished utilizing one or more spatially separated X-ray sources and corresponding number of X-ray lenses focusing the divergent X-ray radiation from each source in a single point, and transportation of the secondary radiation to said detector is performed using X-ray lenses focusing secondary radiation on said detector and having a second focus in the point specified.

7. Method according to claim 1, wherein the concentration of X-ray radiation in the concentration zone is accomplished utilizing one or more spatially separated X-ray sources and corresponding number of X-ray lenses focusing the divergent X-ray radiation from each source in a single point and transportation of the secondary radiation to said detector is performed using collimators oriented in such a way that optical axes of their central channels would intersect in the point specified.

8. Method according to claim 1, wherein the step of executing irradiation program includes increasing radiation intensity by broadening radiation spectrum.

9. Method according to claim 1, wherein the step of executing irradiation program includes controlling radiation intensity by changing anode current of any X-ray tube.

10. Method for determination of the malignant neoplasm position utilizing X-ray radiation beams, in which an image of the malignant neoplasm is acquired in the form of a set of spatial coordinates of points, comprising the steps of;
introducing gadolinium-containing substance,
emitting X-ray radiation with energy corresponding to K-edge of gadolinium atoms absorption;
concentrating the X-ray radiation in a concentration zone within a part of patient body containing the malignant neoplasm;
performing transportation of secondary radiation arising in said zone to at least one detector having maximum sensitivity in a spectral region corresponding to $K_\alpha$-radiation one of gadolinium atoms, for providing selective secondary radiation detection;
scanning the part of patient body containing the malignant neoplasm by relative displacement of the concentration zone and the patient body;
performing registration of the secondary radiation excited in the concentration zone using said at least one detector;
when a signal is detected at the output of said at least one detector, registering parameters characterizing spatial position of the concentration zone and a field of view of said at least one detector having a signal at its output,
identifying each region common for the concentration zone and the field of view of said at least one detector having a signal detected at the output as containing cells of the malignant neoplasm; and
determining position of the malignant neoplasm based on the identified regions.

11. Method according to claim 10, wherein the concentration of X-ray radiation in the concentration is accomplished with at least one collimator, and transportation of the secondary radiation to said detector is also performed with one or more collimators, all the collimators being oriented in such a way that axes of their central channels would intersect in a single point.

12. Method according to claim 10, wherein the concentration of X-ray radiation in the concentration zone is accomplished with one or more X-ray half-lenses transforming divergent radiation from corresponding number of spatially separated X-ray sources into quasi-parallel one, and transportation of the secondary radiation to said detector is performed using one or more X-ray half-lenses focusing secondary radiation on said detector or generating a quasi-parallel radiation, all the X-ray half-lenses being oriented in such a way that their optical axes would intersect in a single point.

13. Method according to claim 10, wherein the concentration of X-ray radiation in the concentration zone is accomplished with one or more X-ray half-lenses transforming divergent radiation from corresponding number of spatially separated X-ray sources into quasi-parallel one, and transportation of the secondary radiation to said at least one detector is performed using at least one X-ray lens focusing secondary radiation on said at least one detector, all the X-ray half-lenses and lenses being oriented in such a way that their optical axes would intersect in a single point.

14. Method according to claim 10, wherein the concentration of X-ray radiation in the concentration zone is accomplished with one or more X-ray half-lenses transforming divergent radiation from corresponding number of spatially separated sources into quasi-parallel one, and transportation of the secondary radiation to said detector is performed using one or more collimators, the X-ray half-lenses and collimators being oriented in such a way that optical axes of all X-ray half-lenses and central channels of all collimators would intersect in a single point.

15. Method according to claim 10, wherein the concentration of X-ray radiation in the concentration zone is accomplished using one or more X-ray sources and corresponding number of X-ray lenses focusing divergent X-ray radiation from each of the sources in single point, and transportation of the secondary radiation to said detector is performed using one or more X-ray lenses focusing secondary radiation on said detector and having a second focus in the point specified.

16. Method according to claim 10, wherein the concentration of X-ray radiation in the concentration zone is accomplished using one or more spatially separated X-ray sources and corresponding number of X-ray lenses focusing divergent X-ray radiation from each of the sources in single point, and transportation of the secondary radiation to said detector is performed using collimators, oriented in such a way that optical axes of their central channels would intersect in the point specified.

17. Method for gadolinium detection in tissues and organs of a human body, comprising the steps of:
  emitting X-ray radiation with an energy corresponding to K-edge of gadolinium atoms absorption;
  concentrating the X-ray radiation in a concentration zone of patient body comprising tissues and organs presumably containing gadolinium;
  performing transportation of secondary radiation arising in said zone to at least one detector having maximum sensitivity in a spectral region corresponding to $K_\alpha$-radiation of gadolinium atoms, for providing selective secondary radiation detection;
  performing registration of the secondary radiation excited in the concentration zone using said at least one detector;
  when a signal is detected at the output of said at least one detector, registering parameters characterizing spatial position of the concentration zone and a field of vision of said at least one detector with a signal detected at the output, and
  identifying each region common for the concentration zone and the field of vision of said at least one detector having a signal detected at the output as containing gadolinium.

18. Method according to claim 17, wherein the concentration of X-ray radiation in the concentration zone is performed using at least one X-ray source and at least one X ray lens for focusing divergent X-ray radiation from the X-ray source in single point, and transportation of the secondary radiation to said at least one detector is performed using at least one X-ray lens focusing said radiation on said at least one detector and having a second focus in the point specified.

19. Device for detecting gadolinium presence in tissues and organs of human body utilizing X-ray radiation beams, comprising:
  a roentgenooptical system having at least one X-ray source for generating X-ray radiation with energy corresponding to K-edge of gadolinium atoms absorption, and at least one concentration element for concentrating X-ray radiation in a concentration zone within a portion of a patient body containing gadolinium;
  at least one detector having maximum sensitivity in a spectral region corresponding to $K_\alpha$-radiation of gadolinium atoms, for providing selective secondary radiation detection;
  at least one transportation element for transporting secondary radiation produced in the concentration zone to said at least one detector, optical axes of said at least one concentration element and said at least one transportation element intersecting in a single point in the concentration zone, wherein said at least one detector is prevented from being arranged on a continuation of an optical axis of said at least one concentration element;
  a positioning element for providing relative movement between the patient body and the roentgenooptical system;
  a sensor for determining coordinates of said point in the concentration zone, and
  an information processing unit responsive to said sensor and an output of said at least one detector for determining position of a region in the human body containing gadolinium based on the output of said at least one detector and respective coordinates determined by said sensor when the patient body and the roentgen-ooptical system move with respect to each other.

20. Device according to claim 19, wherein the region in the human body containing gadolinium is considered to be a region containing cells of malignant neoplasm, and said at least one X-ray source is configured to provide variable radiation intensity so as to damage the cells of malignant neoplasm using an elevated level of the radiation intensity.

21. Device according to claim 20, wherein the X-ray source is configured to increase radiation intensity by broadening radiation spectrum.

22. Device according to claim 20, wherein the X-ray source is configured to control radiation intensity by changing anode current of an X-ray tube.

23. Device according to claim 20, further comprising means for switching off or shielding said at least one detector during periods of X-ray radiation sources operation at elevated intensity.

24. Device according to any of claims 19 to 23, wherein the concentration element and the transportation element include collimators with channels oriented towards the concentration zone, optical axes of central channels of all the collimators intersecting in said point in the concentration zone.

25. Device according to claim 24, wherein the X-ray source is a quasi-point element, and the collimators have channels focused on the X-ray source, with a shield having an opening being mounted between an output of the X-ray source and an inlet of the collimator.

26. Device according to claim 24, wherein the X-ray source is an extended element ones, and the collimators have channels diverging towards X-ray source.

27. Device according to any of claims 19 to 23, wherein the X-ray source is a quasi-point element, the concentration element is made in the form of X-ray half-lens transforming diverging radiation from the source into a quasi-parallel one, and the transportation element is made in the form of X-ray half-lens focusing secondary radiation on said detector, the optical axes of X-ray half-lenses intersecting in said point in the concentration zone.

28. Device according to any of claims 19 to 23, wherein the X-ray source is a quasi-point element, the concentration element is made in the form of X-ray half-lens transforming diverging radiation from the source into quasi-parallel one, and the transportation element is made in the form of X-ray half-lens forming quasi-parallel radiation and having a focus in the concentration zone, the optical axes of all the X-ray half-lenses intersecting in said point in the concentration zone.

29. Device according to any of claims 19 to 23, wherein the X-ray source is a quasi-point element, the concentration element is made in the form of X-ray half-lens transforming diverging radiation from the source into quasi-parallel one, and the transportation element is made in the form of X-ray lens focusing secondary radiation on said detector and having a second focus in the concentration zone, the optical axes of all the X-ray half-lenses and lenses intersecting in said point in the concentration zone.

30. Device according to any of claims 19 to 23, wherein the X-ray source is a quasi-point element, the concentration element is made in the form of X-ray half-lens transforming diverging radiation from the source into quasi-parallel one, and the transportation element is made in the form of collimator having channels diverging towards the detector, the optical axes of all the X-ray half-lenses and lenses and central channels of the collimator intersecting in said point in the concentration zone.

31. Device according to any of claims 19 to 23, wherein the X-ray source is a quasi-point element, the concentration element is made in the form of X-ray half-lens transforming diverging radiation from the X-ray source into quasi-parallel one, and the transportation element is made in the form of collimator having channels converging towards the detector, the optical axes of all the X-ray half-lenses and central channels of collimators intersecting in said point in the concentration zone.

32. Device according to any of claims 19 to 23, wherein the X-ray source is a quasi-point element, the concentration element made in the form of X-ray lens focusing diverging radiation of X-ray source, and the transportation element is in the form of X-ray lens focusing radiation on the detector, the optical axes of all the X-ray lenses intersecting in said point in the concentration zone.

33. Device according to any of claims 19 to 23, wherein the X-ray source is a quasi-point element, the concentration element is made in the form of X-ray lens focusing diverging radiation of X-ray source, and the transportation element is made in the form of collimator having channels converging towards corresponding detector, the optical axes of all the X-ray lenses and central channels of collimators intersecting in said point in the concentration zone.

34. Device according to any of claims 19 to 23, wherein the X-ray source is a quasi-point element, the concentration element is made in the form of X-ray lens focusing diverging radiation of X-ray, and the transportation element is made in the form of collimator having channels diverging towards corresponding detector, the optical axes of all the X-ray lenses and central channels of collimators intersecting in said point in the concentration zone.

* * * * *